(12) United States Patent
Hagemann et al.

(10) Patent No.: US 6,608,211 B1
(45) Date of Patent: Aug. 19, 2003

(54) SUBSTITUTED PHENYL KETOENOLS

(75) Inventors: Hermann Hagemann, Leverkusen (DE); Reiner Fischer, Monheim (DE); Christoph Erdelen, Leichlingen (DE); Ulrike Wachendorff-Neumann, Neuwied (DE); Udo Schneider, Leverkusen (DE); Wolfram Andersch, Bergisch-Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/530,883

(22) PCT Filed: Oct. 29, 1998

(86) PCT No.: PCT/EP98/06866

§ 371 (c)(1),
(2), (4) Date: May 8, 2000

(87) PCT Pub. No.: WO99/24437

PCT Pub. Date: May 20, 1999

(30) Foreign Application Priority Data

Nov. 11, 1997  (DE) ......................................... 197 49 720

(51) Int. Cl.⁷ ..................... C07D 491/107; A10N 43/90
(52) U.S. Cl. ................... 548/410; 504/116.1; D22/120
(58) Field of Search ...................... 548/410; 504/116.1; D22/120

(56) References Cited

U.S. PATENT DOCUMENTS

| | | | |
|---|---|---|---|
| 5,258,527 A | 11/1993 | Krauskopf et al. | 548/543 |
| 5,462,913 A | 10/1995 | Fischer et al. | 504/138 |
| 5,504,057 A | 4/1996 | Fischer et al. | 504/283 |
| 5,567,671 A | 10/1996 | Fischer et al. | 504/283 |
| 5,589,469 A | 12/1996 | Fischer et al. | 514/491 |
| 5,602,078 A | 2/1997 | Fischer et al. | 504/283 |
| 5,616,536 A | 4/1997 | Fischer et al. | 504/225 |
| 5,677,449 A | 10/1997 | Fischer et al. | 544/165 |
| 5,736,336 A | * 4/1998 | Buchardt et al. | |
| 5,830,826 A | 11/1998 | Fischer et al. | 504/195 |
| 5,847,211 A | 12/1998 | Fischer et al. | 564/123 |
| 5,994,274 A | 11/1999 | Fischer et al. | 504/282 |

FOREIGN PATENT DOCUMENTS

| | | |
|---|---|---|
| DE | 33 14 249 | 10/1984 |
| DE | 4415334 A1 * | 1/1995 |
| DE | 19649665 | 10/1997 |
| DE | 197 49 720 A1 * | 12/1999 |
| WO | 95/01358 | 1/1995 |
| WO | 95/20572 | 8/1995 |
| WO | 96/25385 | 8/1996 |
| WO | 96/35664 | 11/1996 |
| WO | 97/01535 | 1/1997 |

OTHER PUBLICATIONS

Chem. Reviews, vol. 52, (month unavailable) 1953, pp. 237–416,Norman O.V. Sonntag, The Reactions of Aliphatic Acid Chlorides.

Indian J. Chem. 6, (month unavailable) 1968, pp. 341–345, Bhabatosh Bhattacharya, Isoquinoline Derivatives: Part XVIII–Formation of I-Alkyl–(ro alkaryl or aryl)–3–methyl–7–chloro–(or 5–chloro)–isoquinolines.

Chem. Ind. London, Nov. 9, 1968, H.R. Harrison, et al, Use of molecular sieves in the methyl esterification of carboxylic acids.

Organikum, (month unavailable) 1977, p. 505, Reaktionen von Carbonsäuren und Carbonsäurederivaten mit Basen.

Ann. Chim. (Paris), (month unavailable) 1970, P.L. Compagnon et al, pp. 11–22 & 22–37, Addition Des. Réactifs Nucléophiles Sur La Triple Liaison Nitrile.

J. Chem. Soc., (month unavailable) 1961, L. Munday, pp. 4372–4379, amino–acids of the Cyclohexane Series. Part I.

Can. J. Chem. vol. 53, (month unavailable) 1975, pp. 3339–3350, John T. Edward et al Stereochemistry of the Bucherer–Bergs and Strecker Reactions of 4–tert–Butylcyclohexanone.

* cited by examiner

Primary Examiner—T. A. Solola
(74) Attorney, Agent, or Firm—Richard E. L. Henderson; Joseph C. Gil; Raymond J. Harmuth

(57) ABSTRACT

The invention relates to novel phenyl-substituted cyclic ketoenols of the formula (I)

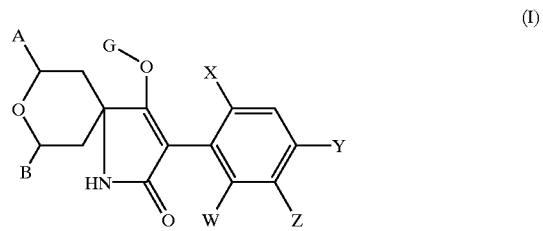

(I)

in which
A, B, G, X, Y, Z and W are each as defined in the description,
to processes and intermediates for their preparation and to their use as pesticides and herbicides.

8 Claims, No Drawings

SUBSTITUTED PHENYL KETOENOLS

This application is a 371 of PCT/EP98/06866 filed Oct. 29, 1998.

The invention relates to novel phenyl-substituted cyclic ketoenols, to a plurality of processes and intermediates for their preparation and to their use as pesticides and herbicides.

It is already known that certain phenyl-substituted cyclic ketoenols are active as insecticides, acaricides and/or herbicides.

1H-Arylpyrrolidine-dione derivatives (EP-A-456 063, EP-A-521 334, EP-A-596 298, EP-A-613 884, EP-A-613 885, DE-44 40594, DE-196 49 665, WO 94/01 997, WO 95/01 358, WO 95/20 572, EP-A-668 267, WO 95/26 954, WO 96/25395, WO 96/35 664, WO 97/01 535 and WO 97/02 243) and their use as pesticides and, of some of them, as herbicides, are known.

However, the herbicidal, acaricidal and insecticidal activity and/or spectrum of activity and/or plant safety of these compounds, in particular with respect to crop plants, is not always satisfactory.

This invention, accordingly, provides novel compounds of the formula (I)

(I)

in which
- W represents hydrogen, cyano, nitro, halogen, alkyl, alkenyl, alkinyl, alkoxy, halogenoalkyl, halogenoalkoxy or represents phenyl, phenoxy, phenylthio, phenylalkoxy or phenylalkylthio, each of which is optionally substituted,
- X represents halogen, alkyl, alkenyl, alkinyl, alkoxy, alkenyloxy, halogenoalkyl, halogenoalkoxy, halogenoalkenyloxy, cyano, nitro or represents phenyl, phenoxy, phenylthio, phenylalkyloxy or phenylalkylthio, each of which is optionally substituted,
- Y represents hydrogen, halogen, alkyl, alkoxy, halogenoalkyl, halogenoalkoxy, cyano or nitro,
- Z represents hydrogen, halogen, alkyl, alkoxy, halogenoalkyl, halogenoalkoxy, hydroxyl, cyano, nitro or represents phenoxy, phenylthio, 5- or 6-membered hetaryloxy, 5- or 6-membered hetarylthio, phenylalkyloxy or phenylalkylthio, each of which is optionally substituted,
- A represents alkyl or optionally substituted phenyl,
- B represents hydrogen or alkyl,
- G represents hydrogen (a) or one of the radicals (b)

-continued (c)

(d)

(e)

(f)

E, or (g)

in which
- E represents a metal ion equivalent or an ammonium ion,
- L represents oxygen or sulphur,
- M represents oxygen or sulphur,
- $R^1$ represents alkyl, alkenyl, alkoxyalkyl, alkylthioalkyl or polyalkoxyalkyl, each of which is optionally substituted by halogen or cyano, or represents cycloalkyl or heterocyclyl, each of which is optionally substituted by halogen, alkyl or alkoxy, or represents phenyl, phenylalkyl, hetaryl, phenoxyalkyl or hetaryloxyalkyl, each of which is optionally substituted,
- $R^2$ represents alkyl, alkenyl, alkoxyalkyl or polyalkoxyalkyl, each of which is optionally substituted by halogen or cyano, or represents cycloalkyl, phenyl or benzyl, each of which is optionally substituted,
- $R^3$, $R^4$ and $R^5$ independently of one another each represent alkyl, alkoxy, alkylamino, dialkylamino, alkylthio, alkenylthio or cycloalkylthio, each of which is optionally substituted by halogen, or represent phenyl, benzyl, phenoxy or phenylthio, each of which is optionally substituted,
- $R^6$ and $R^7$ independently of one another each represent hydrogen, represent alkyl, cycloalkyl, alkenyl, alkoxy, alkoxyalkyl, each of which is optionally substituted by halogen or cyano, represent phenyl or benzyl, each of which is optionally substituted, or together with the linking N atom form a cycle which optionally contains oxygen or sulphur and which is optionally substituted.

The compounds of the formula (I) can he present, depending, inter alia, on the nature of the substituents, as optical isomers or isomer mixtures of differing composition which, if appropriate, can be separated in a customary manner. Both the pure isomers and the isomer mxtures, their preparation and use, and compositions comprising them are part of the subject matter of the present invention. In the following, for simplicity, however, compounds of the formula (I) are always referred to, although both pure compounds and, if appropriate, mixtures having different proportions of isomeric compounds are intended.

Including the various meanings (a), (b), (c), (d), (e), (f) and (g) of the group G, the following principal structures (I-a) to (I-g) result:

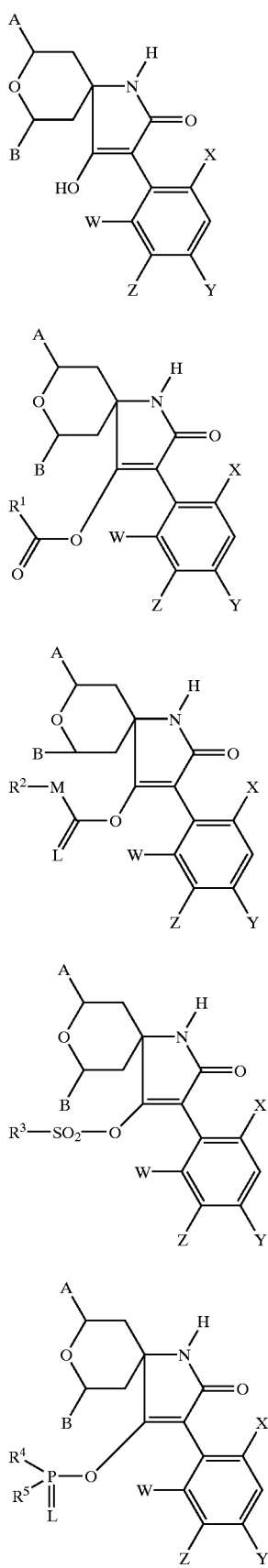
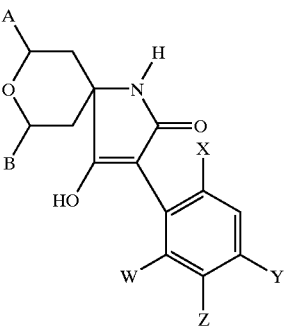
in which
A, B, E, L, M, W, X, Y, Z, $R^1$, $R^2$, $R^3$, $R^4$, $R^5$, $R^6$ and $R^7$ are each as defined above.
Furthermore, it has been found that the novel compounds of the formula (I) are obtained by one of the processes described below:
(A) compounds of the formula (I-a)
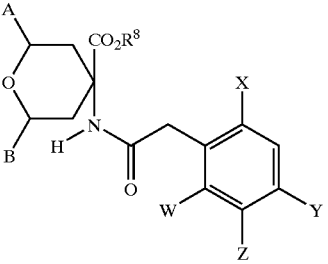
in which
A, B, W, X, Y and Z, are each as defined above, are obtained when
compounds of the formula (II)

in which

A, B, W, X, Y and Z are each as defined above, and

R$^8$ represents alkyl (preferably C$_1$–C$_6$-alkyl), are intramolecularly condensed in the presence of a diluent and in the presence of a base.

Furthermore, it has been found (B) that the compounds of the formula (I-b) shown above in which R$^1$, A, B, W, X, Y and Z are each as defined above are obtained when compounds of the formula (I-a) shown above in which A, B, W, X, Y and Z are each as defined above, α) are reacted with acyl halides of the formula (III)

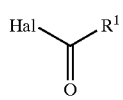

(III)

in which

R$^1$ is as defined above and

Hal represents halogen (in particular chlorine or bromine) or

β) are reacted with carboxylic anhydrides of the formula (IV)

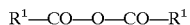

(IV)

in which

R$^1$ is as defined above, if appropriate in the presence of a diluent and if appropriate in the presence of an acid binder;

(C) that the compounds of the formula (I-c) shown above in which R$^2$, A, B, W, M, X, Y and Z are each as defined above and L represents oxygen are obtained when compounds of the formula (I-a) shown above in which A, B, W, X, Y and Z are each as defined above, are reacted with chloroformic esters or chloroformic thioesters of the formula (V)

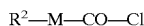

(V)

in which

R$^2$ and M are each as defined above, if appropriate in the presence of a diluent and if appropriate in the presence of an acid binder;

(D) that compounds of the formula (I-c) shown above in which R$^2$, A, B, W, M, X, Y and Z are each as defined above and L represents sulphur are obtained when compounds of the formula (I-a) shown above in which A, B, W, X, Y and Z are each as defined above, are reacted with chloromonothioformic esters or chlorodithioformic esters of the formula (VI)

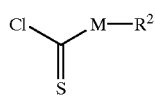

(VI)

in which

M and R$^2$ are each as defined above, if appropriate in the presence of a diluent and if appropriate in the presence of an acid binder;

(E) that compounds of the formula (I-d) shown above in which R$^3$, A, B, W, X, Y and Z are each as defined above are obtained when compounds of the formula (I-a) shown above in which A, B, W, X, Y and Z are each as defined above, are reacted with sulphonyl chlorides of the formula (VII)

(VII)

in which

R$^3$ is as defined above, if appropriate in the presence of a diluent and if appropriate in the presence of an acid binder, (F) that compounds of the formula (I-e) shown above in which L, R$^4$, R$^5$, A, B, W, X, Y and Z are each as defined above are obtained when compounds of the formula (I-a) shown above in which A, B, W, X, Y and Z are each as defined above, are reacted with phosphorus compounds of the formula (VIII)

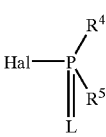

(VIII)

in which

L, R$^4$ and R$^5$ are each as defined above and

Hal represents halogen (in particular chlorine or bromine), if appropriate in the presence of a diluent and if appropriate in the presence of an acid binder;

(G) that compounds of the formula (I-f) shown above in which E, A, B, W, X, Y and Z are each as defined above are obtained when compounds of the formula (I-a) in which A, B, W, X, Y and Z are each as defined above, are reacted with metal compounds or amines of the formulae (IX) or (X)

(IX)

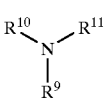

(X)

in which

Me represents a mono- or divalent metal (preferably an alkali metal or alkaline earth metal such as lithium, sodium, potassium, magnesium or calcium), t represents the number 1 or 2 and R$^9$, R$^{10}$, R$^{11}$ independently of one another each represent hydrogen or alkyl (preferably C$_1$–C$_8$-alkyl), if appropriate in the presence of a diluent;

(H) that compounds of the formula (I-g) shown above in which L, R$^6$, R$^7$, A, B, W, X, Y and Z are each as defined above are obtained when compounds of the formula (I-a) shown above in which A, B, W, X, Y and Z are each as defined above, α) are reacted with isocyanates or isothiocyanates of the formula (XI)

(XI)

in which

R$^6$ and L are each as defined above, if appropriate in the presence of a diluent and if appropriate in the presence of a catalyst, or β) are reacted with carbamoyl chlorides or thiocarbamoyl chlorides of the formula (XII)

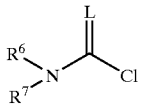
(XII)

in which

L, $R^6$ and $R^7$ are each as defined above, if appropriate in the presence of a diluent and if appropriate in the presence of an acid binder.

Furthermore, it has been found that the novel compounds of the formula (I) have very good activity as pesticides, preferably as insecticides and as acaricides, and as herbicides, and that they are additionally frequently very well tolerated by plants, in particular by crop plants.

The formula (I) provides a general definition of the compounds according to the invention. Preferred substituents and/or ranges of the radicals listed in the formula mentioned hereinabove and hereinbelow are illustrated below:

W preferably represents hydrogen, nitro, cyano, halogen, $C_1$–$C_6$-alkyl, $C_2$–$C_6$-alkenyl, $C_2$–$C_6$-alkinyl, $C_1$–$C_6$-alkoxy, $C_1$–$C_4$-halogenoalkyl or $C_1$–$C_4$-halogenoalkoxy.

X preferably represents halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_4$-halogenoalkyl, $C_1$–$C_4$-halogenoalkoxy, $C_2$–$C_6$-halogenoalkenyloxy, cyano, nitro or represents phenyl, phenoxy, phenylthio, phenyl-$C_1$–$C_4$-alkoxy or phenyl-$C_1$–$C_4$-alkylthio, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

Y preferably represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

Z preferably represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, hydroxyl, cyano, nitro or represents phenoxy, phenylthio, thiazolyloxy, pyridinyloxy, pyrimidyloxy, pyrazolyloxy, phenyl-$C_1$–$C_4$-alkyloxy or phenyl-$C_1$–$C_4$-alkylthio, each of which is optionally substituted by halogen, $C_1$–$C_4$-alkyl, $C_1$–$C_4$-alkoxy, $C_1$–$C_4$-halogenoalkyl, $C_1$–$C_4$-halogenalkoxy, nitro or cyano.

A preferably represents $C_1$–$C_6$-alkyl or represents phenyl which is optionally substituted by halogen, $C_1$–$C_4$-alkyl, $C_1$–$C_4$-alkoxy, nitro or cyano.

B preferably represents, hydrogen or $C_1$–$C_6$-alkyl.

G preferably represents hydrogen (a) or represents one of the radicals

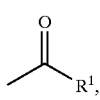
(b)

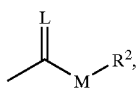
(c)

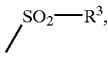
(d)

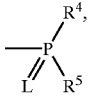
(e)

E,  or (f)

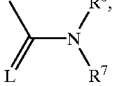
(g)

in which

E represents a metal ion equivalent or an ammonium ion,

L represents oxygen or sulphur and

M represents oxygen or sulphur.

$R^1$ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which is optionally substituted by halogen or cyano, or represents $C_3$–$C_8$-cycloalkyl in which optionally one or two not directly adjacent methylene groups are replaced by oxygen and/or sulphur and which is optionally substituted by halogen, $C_1$–$C_6$-alkyl or $C_1$–$C_6$-alkoxy, represents phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulfonyl, represents phenyl-$C_1$–$C_6$-alkyl which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, represents 5- or 6-membered hetaryl having one or two hetero atoms selected from the group consisting of oxygen, sulphur and nitrogen (for example pyrazolyl, thiazolyl, pyridyl, pyrimidyl, furanyl or thienyl) which is optionally substituted by halogen or $C_1$–$C_6$-alkyl, represents phenoxy-$C_1$–$C_6$-alkyl which is optionally substituted by halogen or $C_1$–$C_6$-alkyl or represents 5- or 6-membered hetaryloxy-$C_1$–$C_6$-alkyl having one or two hetero atoms selected from the group consisting of oxygen, sulphur and nitrogen (for example pyridyloxy-$C_1$–$C_6$-alkyl, pyrimidyloxy-$C_1$–$C_6$-alkyl or thiazolyloxy-$C_1$–$C_6$-alkyl) which is optionally substituted by halogen, amino or $C_1$–$C_6$-alkyl.

$R^2$ preferably represents $C_1$–$C_{20}$-alkyl, $C_2$–$C_{20}$-alkenyl, $C_1$–$C_8$-alkoxy-$C_1$–$C_8$-alkyl or poly-$C_1$–$C_8$-alkoxy-$C_2$–$C_8$-alkyl, each of which is optionally substituted by halogen or cyano, represents $C_3$–$C_8$-cycloalkyl which is optionally substituted by halogen, $C_1$–$C_6$-alkyl or $C_1$–$C_6$-alkoxy or represents phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy.

$R^3$ preferably represents $C_1$–$C_8$-alkyl which is optionally substituted by halogen or represents phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^4$ and $R^5$ independently of one another each preferably represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_3$–$C_8$-alkenylthio, each of which is optionally substituted by halogen, or represents phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another each preferably represent hydrogen, represent $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_2$–$C_8$-alkyl, each of which is optionally substituted by halogen or cyano or represents phenyl or benzyl, each of which is optionally substituted by halogen, $C_1$–$C_8$-alkyl, $C_1$–$C_8$-halogenoalkyl or $C_1$–$C_8$-alkoxy, or together represent a $C_3$–$C_6$-alkylene radical in which optionally one methylene group is replaced by oxygen or sulphur and which is optionally substituted by $C_1$–$C_6$-alkyl.

W particularly preferably represents hydrogen, nitro, cyano, fluorine, chlorine, bromine, $C_1$–$C_4$-alkyl, $C_1$–$C_4$-alkoxy, $C_1$–$C_2$-halogenoalkyl or $C_1$–$C_2$-halogenoalkoxy.

X particularly preferably represents fluorine, chlorine, bromine, $C_1$–$C_4$-alkyl, $C_1$–$C_4$-alkoxy, $C_3$–$C_4$-alkenyloxy, $C_1$–$C_2$-halogenoalkyl, $C_1$–$C_2$-halogenoalkoxy, $C_2$–$C_4$-halogenoalkenyloxy, cyano, nitro or represents phenyl or benzyloxy, each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

Y particularly preferably represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

Z particularly preferably represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxyl, cyano, nitro or represents phenoxy or benzyloxy, each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

A particularly preferably represents $C_1$–$C_4$-alkyl or represents phenyl.

B particularly preferably represents hydrogen, methyl or ethyl.

G particularly preferably represents hydrogen (a) or represents one of the radicals

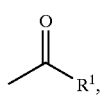 (b)

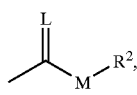 (c)

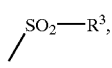 (d)

 (e)

E, or (f)

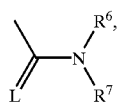 (g)

(in particular represents one of the radicals (a), (b) or (c)), in which

E represents a metal ion equivalent or an ammonium ion,

L represents oxygen or sulphur and

M represents oxygen or sulphur.

$R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl, each of which is optionally substituted by fluorine, chlorine, or represents $C_3$–$C_7$-cycloalkyl in which optionally one or two not directly adjacent methylene groups are replaced by oxygen and/or sulphur and which is optionally substituted by fluorine, chlorine, $C_1$–$C_5$-alkyl or $C_1$–$C_5$-alkoxy, represents phenyl, which is optionally substituted by fluorine, chlorine, bromine, cyano, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl, represents phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, represents pyrazolyl, thiazolyl, pyridyl, pyrimidyl, furanyl or thienyl, each of which is optionally substituted by fluorine, chlorine, bromine or $C_1$–$C_4$-alkyl, represents phenoxy-$C_1$–$C_5$-alkyl which is optionally substituted by fluorine, chlorine, bromine or $C_1$–$C_4$-alkyl or represents pyridyloxy-$C_1$–$C_5$-alkyl, pyrimidyloxy-$C_1$–$C_5$-alkyl or thiazolyloxy-$C_1$–$C_5$-alkyl, each of which is optionally substituted by fluorine, chlorine, bromine, amino or $C_1$–$C_4$-alkyl.

$R^2$ particularly preferably represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, each of which is optionally substituted by fluorine or chlorine, represents $C_3$–$C_7$-cycloalkyl which is optionally substituted by fluorine, chlorine, $C_1$–$C_4$-alkyl or $C_1$–$C_4$-alkoxy or represents phenyl or benzyl, each of which is optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy.

$R^3$ particularly preferably represents $C_1$–$C_6$-alkyl which is optionally substituted by fluorine or chlorine or represents phenyl or benzyl, each of which is optionally substituted by fluorine, chlorine, bromine, $C_1$–$C_4$-alkyl, $C_1$–$C_4$-alkoxy, $C_1$–$C_2$-halogenoalkoxy, $C_1$–$C_2$-halogenoalkyl, cyano or nitro.

$R^4$ and $R^5$ independently of one another particularly preferably represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio, each of which is optionally substituted by fluorine or chlorine, or represent phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another particularly preferably represent hydrogen, represent $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, each of which is optionally substituted by fluorine or chlorine, or represent phenyl or benzyl, each of which is optionally substituted by fluorine, chlorine, bromine, $C_1$–$C_5$-halogenoalkyl, $C_1$–$C_5$-alkyl or $C_1$–$C_5$-alkoxy, or together represent a $C_3$–$C_6$-alkylene radical in which optionally one methylene group is replaced by oxygen or sulphur and which is optionally substituted by $C_1$–$C_4$-alkyl.

In the radical definitions referred to as being (particularly) preferred, halogen in combination with other radicals (for example in halogenoalkyl, halogenoalkoxy or halogenoalkenyloxy) in particular represents fluorine, chlorine and bromine, specifically fluorine and chlorine.

W very particularly preferably represents hydrogen, nitro, cyano, fluorine, chlorine, bromine, methyl, ethyl, n-propyl, isopropyl, n-butyl, isobutyl, methoxy, ethoxy, n-propoxy, isopropoxy, trifluoromethyl, difluoromethoxy or trifluoromethoxy.

X very particularly preferably represents fluorine, chlorine, bromine, methyl, ethyl, n-propyl, isopropyl, n-butyl, isobutyl, methoxy, ethoxy, n-propoxy, isopropoxy, trifluoromethyl, trifluoromethoxy, difluoromethoxy, cyano or nitro.

Y very particularly preferably represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy, difluoromethoxy, cyano or nitro.

Z very particularly preferably represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy, difluoromethoxy, cyano or nitro.

A very particularly preferably represents methyl or ethyl.

B very particularly preferably represents hydrogen or methyl.

G very particularly preferably represents hydrogen (a) or represents one of the radicals

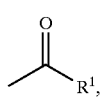
(b)

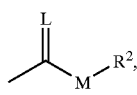
(c)

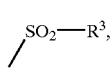
(d)

(e)

E, or
(f)

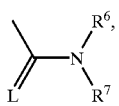
(g)

(in particular represents one of the radicals (a), (b) or (c)), in which

E represents a metal ion equivalent or an ammonium ion,

L represents oxygen or sulphur and

M represents oxygen or sulphur.

$R^1$ very particularly preferably represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl, each of which is optionally substituted by fluorine or chlorine, or represents $C_3$–$C_6$-cycloalkyl in which optionally one or two not directly adjacent methylene groups are replaced by oxygen and/or sulphur and which is optionally substituted by fluorine, chlorine, methyl, ethyl, n-propyl, i-propyl, n-butyl, i-butyl, tert-butyl, methoxy, ethoxy, n-propoxy or isopropoxy, represents phenyl which is optionally substituted by fluorine, chlorine, bromine, cyano, nitro, methyl, ethyl, n-propyl, i-propyl, methoxy, ethoxy, trifluoromethyl, trifluoromethoxy, methylthio, ethylthio, methylsulphonyl or ethylsulphonyl, represents benzyl which is optionally substituted by fluorine, chlorine, bromine, methyl, ethyl, n-propyl, i-propyl, methoxy, ethoxy, trifluoromethyl or trifluoromethoxy, represents furanyl, thienyl or pyridyl, each of which is optionally substituted by fluorine, chlorine, bromine, methyl or ethyl, represents phenoxy-$C_1$–$C_4$-alkyl which is optionally substituted by fluorine, chlorine, methyl or ethyl or represents pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl.

$R^2$ very particularly preferably represents $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, each of which is optionally substituted by fluorine or chlorine, represents $C_3$–$C_6$-cycloalkyl which is optionally substituted by fluorine, chlorine, methyl, ethyl, n-propyl, isopropyl or methoxy, or represents phenyl or benzyl, each of which is optionally substituted by fluorine, chlorine, cyano, nitro, methyl, ethyl, n-propyl, i-propyl, methoxy, ethoxy, trifluoromethyl or trifluoromethoxy.

$R^3$ very particularly preferably represents methyl, ethyl, n-propyl, isopropyl, n-butyl, tert-butyl, each of which is optionally substituted by fluorine or chlorine, or represents phenyl or benzyl, each of which is optionally substituted by fluorine, chlorine, bromine, methyl, ethyl, isopropyl, tert-butyl, methoxy, ethoxy, isopropoxy, trifluoromethyl, trifluoromethoxy, cyano or nitro.

$R^4$ and $R^5$ independently of one another each very particularly preferably represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio, each of which is optionally substituted by fluorine or chlorine, or represent phenyl, phenoxy or phenylthio, each of which is optionally substituted by fluorine, chlorine, bromine, nitro, cyano, methyl, methoxy, trifluoromethyl or trifluoromethoxy.

$R^6$ and $R^7$ independently of one another each very particularly preferably represent hydrogen, represent $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_2$–$C_4$-alkyl, each of which is optionally substituted by fluorine or chlorine, or represent phenyl or benzyl, each of which is optionally substituted by fluorine, chlorine, bromine, methyl, methoxy or trifluoromethyl, or together represent a $C_5$–$C_6$-alkylene radical in which optionally one methylene group is replaced by oxygen or sulphur and which is optionally substituted by methyl or ethyl.

Especially preferred are compounds of the formula (I), in which A represents $CH_3$ and B represents hydrogen, in particular in combination with the very particularly preferred radicals mentioned for G.

The abovementioned general or preferred definitions of radicals or illustrations can be combined with each other as desired, that is to say combinations between the ranges and preferred ranges in question are also possible. They apply both to the end products and, correspondingly, to the starting materials and intermediates. Preference according to the invention is given to those compounds of the formula (I) which contain a combination of the definitions given above as being preferred (preferable).

Particular preference according to the invention is given to those compounds of the formula (I) which contain a combination of the definitions given above as being particularly preferred.

Very particular preference according to the invention is given to those compounds of the formula (I) which contain a combination of the definitions given above as being very particularly preferred.

Saturated or unsaturated hydrocarbon radicals such as alkyl or alkenyl may be, also in connection with hetero atoms such as, for example, in alkoxy, in each case straight-chain or branched as;far as this is possible.

Optionally substituted radicals may be mono- or polysubstituted, it being possible for the substituents in the case of polysubstitutions to be identical or different.

In addition to the compounds mentioned in the Preparation Examples, the following compounds of the formula (I-a) may be mentioned specifically:

TABLE 1

A = $CH_3$; B = H (I-a)

| X | W | Y | Z |
|---|---|---|---|
| Br | H | Cl | H |
| Cl | H | Br | H |
| Cl | H | Cl | H |

TABLE 1-continued

A = $CH_3$; B = H (I-a)

| X | W | Y | Z |
|---|---|---|---|
| Cl | H | F | H |
| F | H | Cl | H |
| Cl | H | $OCH_3$ | H |
| Cl | H | $CH_3$ | H |
| $OCH_3$ | H | Cl | H |
| $OCH_3$ | H | $OCH_3$ | H |
| $CH_3$ | H | Cl | H |
| $CH_3$ | H | F | H |
| $CH_3$ | H | $OCH_3$ | H |
| $CH_3$ | H | t-$C_4H_9$ | H |
| $CH_3$ | H | $CH_3$ | H |
| Cl | Cl | H | H |
| Cl | F | H | H |
| Cl | $OCH_3$ | H | H |
| Cl | CH | H | H |
| Cl | $OC_2H_5$ | H | H |
| $OCH_3$ | $OCH_3$ | H | H |
| $CH_3$ | $CH_3$ | H | H |
| Br | $CH_3$ | Br | H |
| Cl | Cl | $CH_3$ | H |
| $CH_3$ | Br | $CH_3$ | H |
| $CH_3$ | Cl | $CH_3$ | H |
| $CH_3$ | $OCHF_2$ | $CH_3$ | H |
| $CH_3$ | $OCH_2CF_3$ | $CH_3$ | H |
| $CH_3$ | $OC_2H_5$ | $CH_3$ | H |
| $CH_3$ | $OCH_3$ | $CH_3$ | H |
| $CH_3$ | $CH_3$ | $CH_3$ | H |
| Br | Br | $CH_3$ | H |
| Cl | Cl | $CH_3$ | H |
| $C_2H_5$ | $C_2H_5$ | Br | H |
| $CH_3$ | $CH_3$ | Br | H |
| $CH_3$ | $CH_3$ | $OCH_3$ | H |
| Br | Cl | $CH_3$ | H |
| Br | $CH_3$ | Cl | H |
| Cl | $CH_3$ | Br | H |
| $C_2H_5$ | Br | $CH_3$ | H |
| $CH_3$ | O-$C_3H_7$ | $CH_3$ | H |
| $CH_3$ | $CH_3$ | Cl | H |
| Cl | H | Cl | Cl |
| $CH_3$ | H | $CH_3$ | $CH_3$ |
| $CH_3$ | H | Cl | $CH_3$ |
| Br | H | Cl | $CH_3$ |
| Br | H | $CH_3$ | $CH_3$ |
| Cl | H | Br | $CH_3$ |
| Cl | H | Cl | $CH_3$ |
| $CH_3$ | H | Br | $CH_3$ |
| Cl | H | Cl | F |
| Cl | H | $CH_3$ | Cl |
| $CH_3$ | H | H | H |
| Cl | H | H | H |
| Br | H | H | H |
| $CF_3$ | H | H | H |
| $OCH_3$ | H | H | H |
| $CH_3$ | $CH_3$ | $CH_3$ | $CH_3$ |
| $CH_3$ | H | $CH_3$ | $CH_3$ |
| $CH_3$ | $CH_3$ | H | $CH_3$ |
| $CH_3$ | $CH_3$ | $CH_3$ | F |
| $CH_3$ | $CH_3$ | $CH_3$ | Cl |
| $CH_3$ | $CH_3$ | $CH_3$ | Br |
| $CH_3$ | $CH_3$ | H | Cl |
| $CH_3$ | $CH_3$ | H | Br |
| Cl | Cl | H | Br |

Using according to process (A) N-[(4-chloro-2,6-dimethyl)-phenylacetyl]-4-amino-4-carboxyethyl-2-methyl-tetrahydropyran as starting material, the course of the process according to the invention can be represented by the following equation:

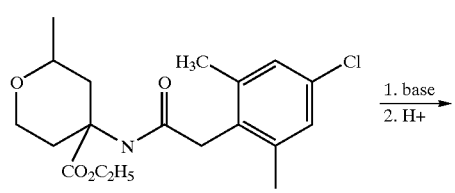

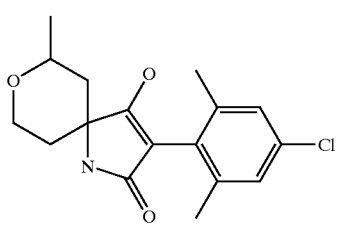

Using according to process (Bα) 3-[(2-chloro-4-methyl)-phenyl]-5,5-[(2-ethyl)-ethyleneoxyethyl]-pyrrolidine-2,4-dione and pivaloyl chloride as starting materials, the course of the process according to the invention can be represented by the following equation:

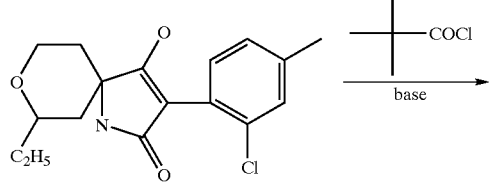
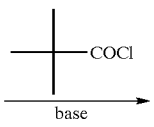

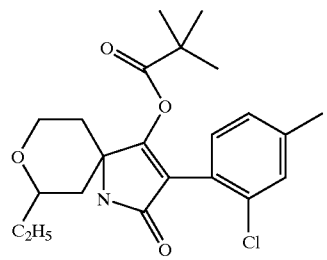

Using according to process (B) (variant β) 3-[(2,4-dichloro)-phenyl]-5,5-[(2-methyl)-ethyleneoxyethyl]-pyrrolidine-2,4-dione and acetic anhydride as starting materials, the course of the process according to the invention can be represented by the following equation:

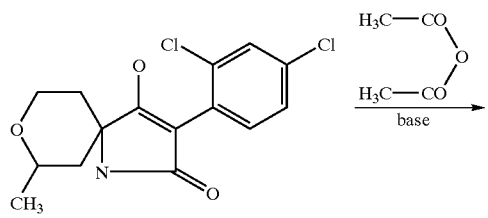
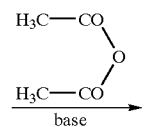

-continued

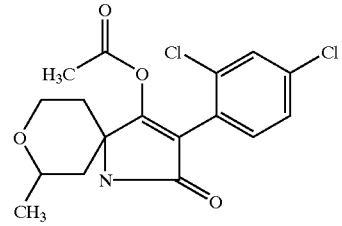

Using according to process (C) 8-[(2,4-dichloro)-phenyl]-5,5-[(2-methyl)-ethylene-oxyethyl]-pyrrolidine-2,4-dione and ethoxyethyl chloroformate as starting materials, the course of the process according to the invention can be represented by the following equation:

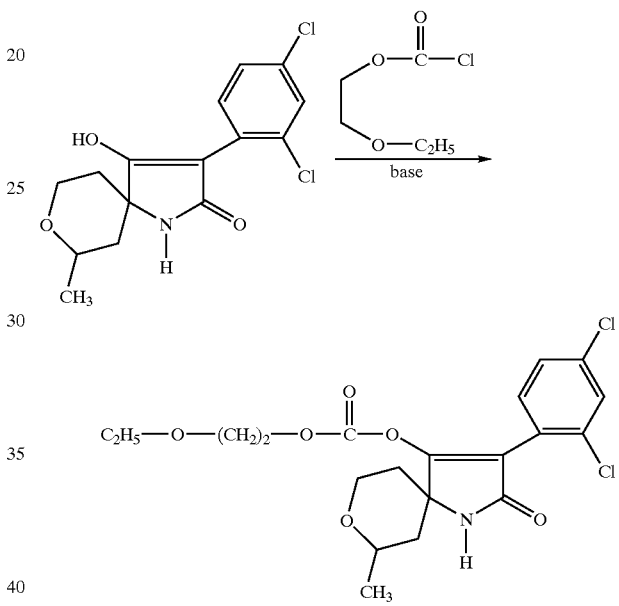

Using according to process (D) 3-[(2,6-dibromo-4-methyl)-phenyl]-5,5-[(2-ethyl)-ethyleneoxyethyl]-pyrrolidine-2,4-dione and methyl chloromonothioformate as starting materials, the course of the reaction can be represented as follows:

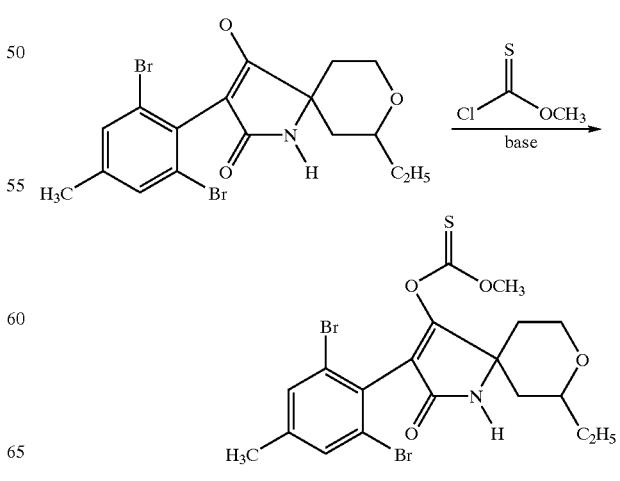

Using according to process (E) 2-[(2,4,6-trimethyl)-phenyl]-5,5-[(2-methyl)-ethyleneoxyethyl]-pyrrolidine-2,4-dione and methanesulphonyl chloride as starting materials, the course of the reaction can be represented by the following equation:

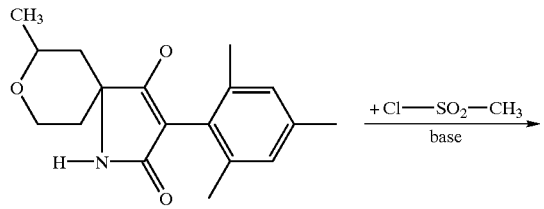

Using according to process (F) 2-[(4-bromo-2-chloro-6-methyl)-phenyl]-4-hydroxy-5,5-[(2-methyl)-ethyleneoxyethyl]-pyrrolidine-2,4-dione and (2,2,2-trifluoroethyl) methanethio-phosphonyl chloride as starting materials, the course of the reaction can be represented by the following equation:

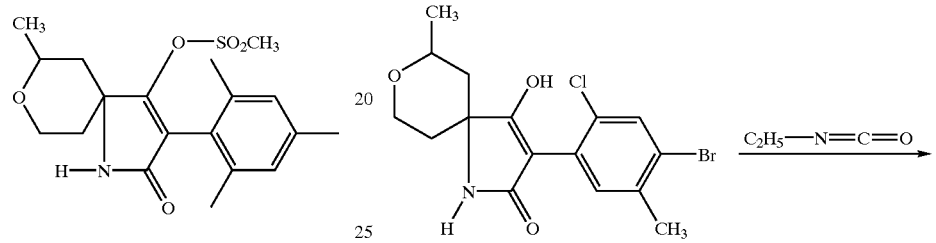

Using according to process (G) 3-[(2,4-dichloro)-6-methylphenyl]-5,5-[(2-ethyl)-ethyleneoxyethyl]-pyrrolidine-2,4-dione and NaOH as components, the course of the process according to the invention can be represented by the following equation:

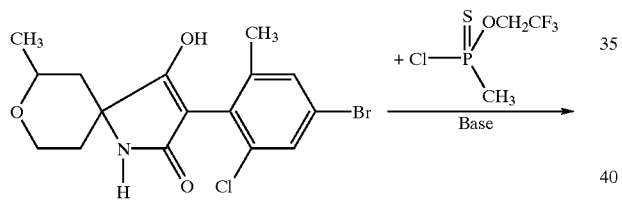

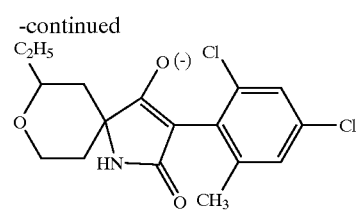

Using according to process (H) (variant α) 3-[(2-chloro-4-bromo-5-methyl)-phenyl]-4-hydroxy-5,5-[(2-methyl)-ethyleneoxyethyl]-pyrrolidine-2,4-dione and ethyl isocyanate as starting materials, the course of the reaction can be represented by the following equation:

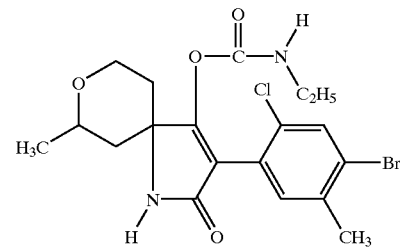

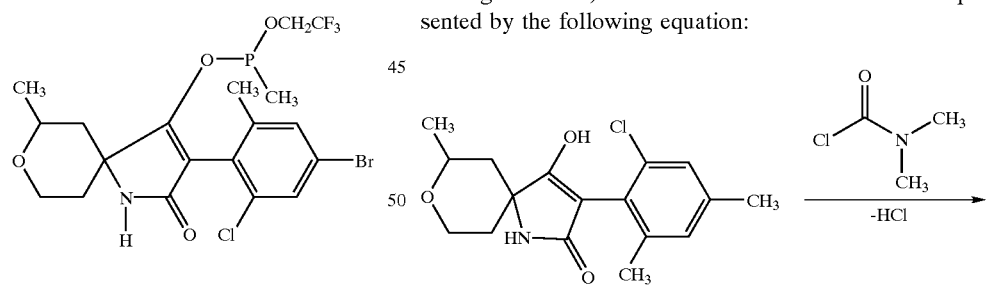

Using according to process (H) (variant β) 3-[(2-chloro-4,6-dimethyl)-phenyl]-5,5-[(2-methyl)-ethyleneoxyethyl]-pyrrolidine-2,4-dione and dimethylcarbamidoyl chloride as starting materials, the course of the reaction can be represented by the following equation:

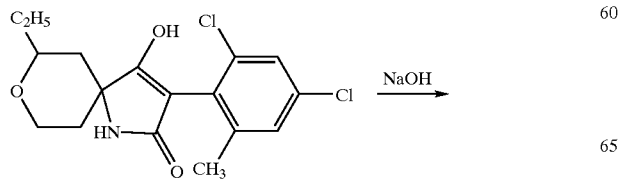

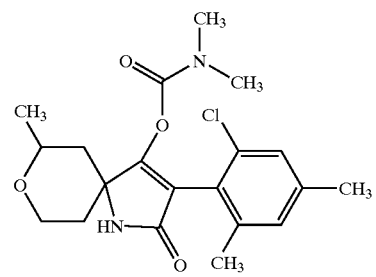

The compounds of the formula (II) required as starting materials in the process (A) according to the invention

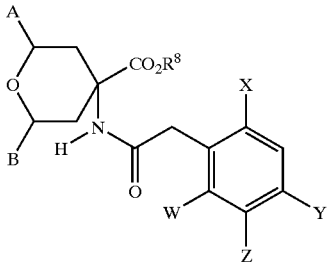

(II)

in which
A, B, W, X, Y, Z and R⁸ are each as defined above,
are novel.

The acylamino acid esters of the formula (II) are obtained, for example, when amino acid derivatives of the formula (XIII)

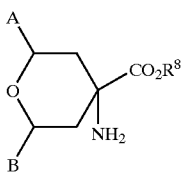

(XIII)

in which
A, B and R⁸ are each as defined above,
are acylated with substituted phenylacetyl halides of the formula (XIV)

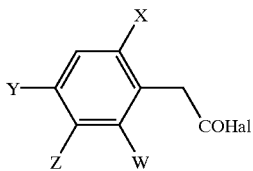

in which
W, X, Y and Z are each as defined above and
Hal represents chlorine or bromine,
(Chem. Reviews 52, 237–416 (1953); Bhattacharya, Indian J. Chem. 6, 341–5, 1968)
or when acylamino acids of the formula (XV)

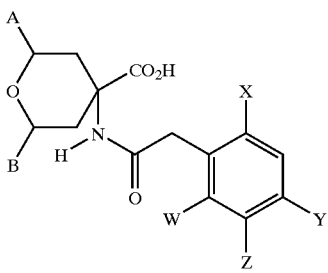

(XV)

in which
A, B, W, X, Y and Z are each as defined above,
are esterified (Chem. Ind. (London) 1568 (1968)).

The compounds of the formula (XV)

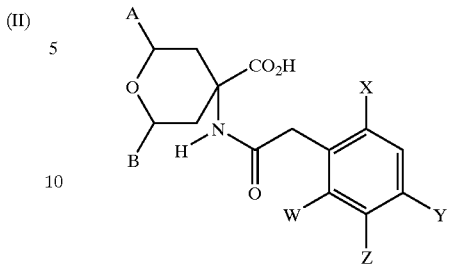

(XV)

in which
A, B, W, X, Y and Z are each as defined above,
are novel.

The compounds of the formula (XV) are obtained, for example, when 4-amino-tetrahydropyran-4-carboxylic acids of the formula (XVI)

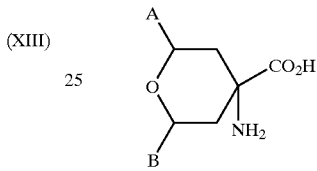

(XVI)

in which
A and B are each as defined above
are acylated according to Schotten-Baumann (Organikum, VEB Deutscher Verlag der Wissenschaften, Berlin 1977, P. 505) with substituted phenylacetyl halides of the formula (XIV)

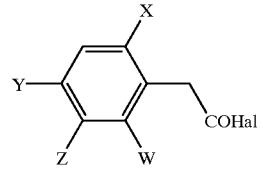

(XIV)

in which
W, X, Y and Z are each as defined above and
Hal represents chlorine or bromine.

Some of the compounds of the formula (XIV) are novel and can be prepared by known processes (cf., for example, DE-196 49 665).

The compounds of the formula (XIV) are obtained, for example, by reacting substituted phenylacetic acids of the formula (XVII)

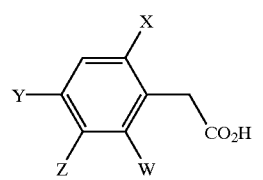

(XVII)

in which
W, X, Y and Z are each as defined above
with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons such as toluene or methylene chloride) at temperatures of from −20° C. to 150° C., preferably of from −10° C. to 100° C.

Some of the compounds of the formula (XVII) are novel, they can be prepared by processes known from the literature (Organikum 15th edition, p. 533. VEB Deutscher Verlag der Wissenschaften, Berlin 1977, cf., for example, DE-196 49 665).

The compounds of the formula (XVII) are obtained, for example, by hydrolysing substituted phenylacetic esters of the formula (XVIII)

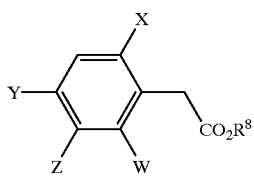

(XVIII)

in which

W, X, Y, Z and $R^8$ are each as defined above in the presence of an acid (for example an inorganic acid such as hydrochloric acid) or a base (for example an alkali metal hydroxide such as sodium hydroxide or potassium hydroxide) and, if appropriate, a diluent (for example an aqueous alcohol such as methanol or ethanol) at temperatures between 0° C. and 150° C., preferably between 20° C. and 100° C.

Some of the compounds of the formula (XVIII) are novel, they can be prepared by processes known in principle.

The compounds of the formula (XVIII) are obtained, for example, by reacting substituted 1,1,1-trichloro-2-phenylethanes of the formula (XIX)

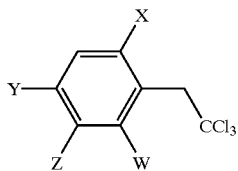

(XIX)

in which

W, X, Y and Z are each as defined above initially with alkoxides (for example alkali metal alkoxides such as sodium methoxide or sodium ethoxide) in the presence of a diluent (for example of the alcohol derived from the alkoxide) at temperatures between 0° C. and 150° C., preferably between 20° C. and 120° C., and subsequently reacting with an acid (preferably an inorganic acid, such as, for example, sulphuric acid) at temperatures between −20° C. and 150° C., preferably between 0° C. and 100° C. (cf. DE-3 314 249).

Some of the compounds of the formula (XIX) are novel, they can be prepared by processes known in principle.

The compounds of the formula (XIX) are obtained, for example, when anilines of the formula (XX)

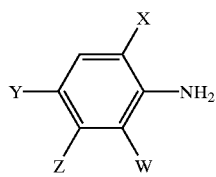

(XX)

in which

W, X, Y and Z are each as defined above are reacted in the presence of alkyl nitrite of the formula (XXI)

$R^{13}$—ONO     (XXI)

in which $R^{13}$ represents alkyl, preferably $C_1$–$C_6$-alkyl, in the presence of copper(II) chloride and if appropriate in the presence of a diluent (for example an aliphatic nitrile such as acetonitrile) at a temperature of from −20° C. to 80° C., preferably of from 0° C. to 60° C., with vinylidene chloride ($CH_2$=$CCl_2$).

Some of the compounds of the formula (XX) are known. They can be prepared by processes known from the literature, for example by reduction of the corresponding nitro compounds or halogenation of the anilines or acetanilides and subsequent recleavage.

The compounds of the formula (XXI) are known compounds of organic chemistry. Copper(II) chloride and vinylidene chloride have been known for a long time and are commercially available.

The substituted cyclic aminocarboxylic acids of the formula (XVI) are generally obtainable by the Bucherer-Bergs synthesis or by the Strecker synthesis and are in each case obtained in these syntheses in different isomer forms. Thus, under the conditions of the Bucherer-Bergs synthesis, the isomers (for simplicity called β below), in which the radicals R and the carboxyl group are equatorial are predominantly obtained, while under the conditions of the Strecker synthesis the isomers (for simplicity called α below) in which the amino group and the radicals R are equatorial are predominantly obtained.

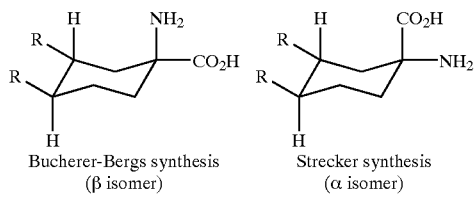

Bucherer-Bergs synthesis (β isomer)          Strecker synthesis (α isomer)

The compounds of the formula (XIII) and (XVI) are novel. They can be prepared by known processes (see, for example, Compagnon, Ann. Chim. (Paris) [14]5, p. 11–22, 23–27 (1970), L. Munday, J. Chem. Soc. 4372 (1961); J. T. Edward, C. Jitrangeri, Can. J. Chem. 53, 3339 (1975)).

Furthermore, the starting materials of the formula (II)

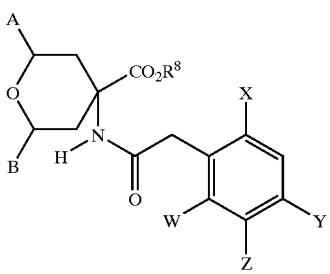

(II)

in which
A, B, W, X, Y, Z and $R^8$ are each as defined above,
used in the above process (A) can be prepared when aminonitriles of the formula (XXII)

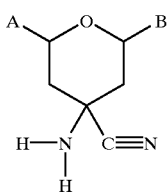

(XXII)

in which
A and B are each as defined above,
are reacted with substituted phenylacetyl halides of the formula (XIV)

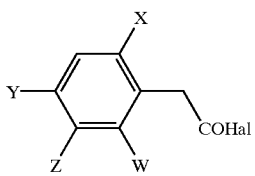

(XIV)

in which
W, X, Y, Z and Hal are each as defined above
to give compounds of the formula (XXIII)

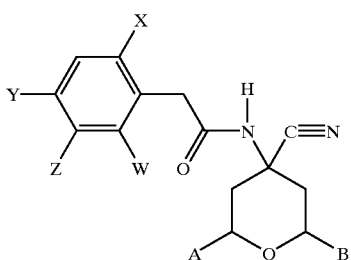

(XXIII)

in which
A, B, W, X, Y and Z are each as defined above
and these are subsequently subjected to acid alcoholysis.

The compounds of the formula (XXIII) are also novel.
The compounds of the formula (XXII) are also novel.
The acyl halides of the formula (III), carboxylic anhydrides of the formula (IV), chloroformic esters or chloroformic thioesters of the formula (V), chloromonothioformic esters or chliorodithioformic esters of the formula (VI), sulphonyl chlorides of the formula (VII), phosphorus compounds of the formula (VIII) and metal hydroxides, metal alkoxides or amines of the formula (IX) and (X) and isocyanates of the formula (XI) and carbamoyl chlorides of the formula (XII) furthermore required as starting materials for carrying out the processes (B), (C), (D), (E), (F), (G) and (H) according to the invention are generally known compounds of organic or inorganic chemistry.

The compounds of the formulae (XIV), (XVII), (XVIII), (XIX) and (XX) are furthermore known from the patent applications cited at the outset and/or can be prepared by the methods given therein (cf. also DE-196 49 665 and the Applicant's German Patent Application having file reference 19613171.5 dated Feb. 4, 1996, which has not yet been laid open).

The process (A) is characterized in that compounds of the formula (II), in which A, B, W, X, Y, Z and $R^8$ are each as defined above are subjected to an intramolecular condensation in the presence of a diluent and in the presence of a base.

Suitable diluents for use in the process (A) according to the invention are all organic solvents which are inert towards the reactants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols such as methanol, ethanol, propanol, isopropanol, butanol, isobutanol and tert-butanol.

Suitable bases (deprotonating agents) for use in the practice of the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase transfer catalysts, such as, for example, triethylbenzylammonium chloride, tetrabutylammonium bromide, Adogen 464 (=methyltrialkyl($C_8$–$C_{10}$) ammonium chloride) or TDA 1 (=tris-(methoxyethoxyethyl) amine). It is also possible to use alkali metals such as sodium or potassium.

Furthermore, it is possible to use alkali metal and alkaline earth metal amides and hydrides, such as sodium amide, sodium hydride and calcium hydride, and moreover also alkali metal alkoxides, such as sodium methoxide, sodium ethoxide and potassium tert-butoxide.

When carrying out the process (A) according to the invention, the reaction temperature can be varied within a relatively wide range. In general, the reaction is carried out at temperatures between –75° C. and 200° C., preferably between –50° C. and 150° C.

The process (A) according to the invention is generally carried out under atmospheric pressure.

When carrying out the process (A) according to the invention, the reaction component of the formula (II) and the deprotonating base are generally employed in equimolar to about doubly-equimolar amounts. However, it is also possible to use one component or the other in a relatively large excess (up to 3 mol).

The process ($B_\alpha$) is characterized in that compounds of the formula (I-a) are reacted with carbonyl halides of the formula (III), if appropriate in the presence of a diluent and if appropriate in the presence of an acid binder.

Suitable diluents for use in the process ($B_\alpha$) according to the invention are all solvents which are inert towards the acyl halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, furthermore ketones, such as acetone and methyl isopropyl ketone, additionally ethers, such as diethyl ether, tetrahydrofuran and dioxane, furthermore, carboxylic esters, such as ethyl acetate, and also strongly polar solvents, such as dimethylformamide, dimethyl sulphoxide and sulpholane. The hydrolytic stability of the acyl halide permitting, the reaction can also be carried out in the presence of water.

Suitable acid binders for the reaction according to the process ($B_\alpha$) according to the invention are all customary acid acceptors. Preference is given to using tertiary amines, such as triethylamine, pyridine, diazabicyclooctane (DABCO), diazabicyclo-undecene (DBU), diazabicyclononene (DBN), Hünig base and N,N-dimethyl-aniline, furthermore alkaline earth metal oxides, such as magnesium oxide and calcium oxide, and also alkali metal and alkaline earth metal carbonates, such as sodium carbonate, potassium carbonate and calcium carbonate and also alkali metal hydroxides such as sodium hydroxide and potassium hydroxide.

The reaction temperature of the process ($B_\alpha$) according to the invention can be varied within a relatively wide range. In general, the reaction is carried out at temperatures between −20° C. and +150° C., preferably between 0° C. and 100° C.

When carrying out the process ($B_\alpha$) according to the invention, the starting materials of the formula (I-a) and the carbonyl halide of the formula (III) are generally each employed in approximately equivalent amounts. However, it is also possible to employ a relatively large excess (up to 5 mol) of the carbonyl halide. Work-up is carried out by customary methods.

The process (Bβ) is characterized in that compounds of the formula (I-a) are reacted with carboxylic anydrides of the formula (IV), if appropriate in the presence of a diluent and if appropriate in the presence of an acid binder.

Suitable diluents for use in the process (Bβ) according to the invention are preferably those diluents which are also preferred when acyl halides are used. Additionally, a carboxylic anhydride employed in excess can also simultaneously act as diluent.

The acid binders which are added in the process (Bβ), if appropriate, are preferably those acid binders which are also preferred when acyl halides are used.

The reaction temperature in the process (Bβ) according to the invention can be varied within a relatively wide range. In general, the reaction is carried out at temperatures between −20° C. and +150° C., preferably between 0° C. and 100° C.

When carrying out the process (Bβ) according to the invention, the starting materials of the formula (I-a) and the carboxylic anhydride of the formula (IV) are generally each employed in approximately equivalent amounts. However, it is also possible to employ a relatively large excess (up to 5 mol) of the carboxylic anhydride. Work-up is carried out by customary methods.

In general, diluent and excess carboxylic anhydride and also the carboxylic acid formed are removed by distillation or by washing with an organic solvent or with water.

The process (C) is characterized in that compounds of the formula (I-a) are reacted with chloroformic esters or chloroformic thiol esters of the formula (V), if appropriate in the presence of a diluent and if appropriate in the presence of an acid binder.

Acid binders which are suitable for the process (C) according to the invention are all customary acid acceptors. Preference is given to using tertiary amines, such as triethylamine, pyridine, DABCO, DBU, DBN, Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides such as sodium hydroxide and potassium hydroxide.

Suitable diluents for use in the process (C) according to the invention are all solvents which are inert towards the chloroformic esters or chloroformic thiol esters. Preference is given to using hydrocarbons, such as benzine, benzene, toluene, xylene and tetralin, furthermore, halogenated hydrocarbons, such as methylene chloride, chloroform, carbon tetrachloride, chlorobenzene and o-dichlorobenzene, furthermore ketones, such as acetone and methyl isopropyl ketone, moreover ethers, such as diethyl ether, tetrahydrofuran and dioxane, furthermore carboxylic esters, such as ethyl acetate, additionally nitriles such as acetonitrile and also strongly polar solvents, such as dimethylformamide, dimethyl sulphoxide and sulpholane.

When carrying out the process (C) according to the invention, the reaction temperature can be varied within a relatively wide range. In general, the reaction temperature is between −20° C. and +100° C., preferably between 0° C. and 50° C.

The process (C) according to the invention is generally carried out under atmospheric pressure.

When carrying out the process (C) according to the invention, the starting materials of the formula (I-a) and the appropriate chloroformic ester or chloroformic thiol ester of the formula (VII) are generally each employed in approximately equivalent amounts. However, it is also possible to employ one component or the other in a relatively large excess (up to 2 mol). Work-up is carried out by customary methods. In general, precipitated salts are removed and the reaction mixture which remains is concentrated by removing the diluent under reduced pressure.

The process (D) according to the invention is characterized in that compounds of the formula (I-a) are reacted with compounds of the formula (VI) in the presence of a diluent and, if appropriate, in the presence of an acid binder.

In the preparation process (D), approximately 1 mol of chloromonothioformic ester or chlorodithioformic ester of the formula (VI) per mole of starting material of the formula (I-a) is reacted at 0 to 120° C., preferably at 20 to 60° C.

Diluents which may be added, if appropriate, are all inert polar organic solvents, such as ethers, amides, sulphones, sulphoxides, and also halogenoalkanes.

Preference is given to using dimethyl sulphoxide, tetrahydrofuran, dimethylformamide, ethyl acetate or methylene chloride.

If, in a preferred embodiment, the enolate salt of the compounds of the formula (I-a) is prepared by addition of strong deprotonating agents such as, for example, sodium hydride or potassium tert-butoxide, the addition of acid binders can be dispensed with.

Suitable bases for use in the process (D) are all customary proton acceptors. Preference is given to using alkali metal hydrides, alkali metal alkoxides, alkali metal or alkaline earth metal carbonates or bicarbonates or nitrogen bases. Examples include sodium hydride, sodium methoxide, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

The reaction can be carried out under atmospheric pressure or under elevated pressure and is preferably carried out under atmospheric pressure. Work-up is carried out by customary methods.

The process (E) according to the invention is characterized in that compounds of the formula (I-a) are in each case reacted with sulphonyl chlorides or the formula (VII), if appropriate in the presence of a diluent and if appropriate in the presence of an acid binder.

In the preparation process (E), approximately 1 mol of sulphonyl chloride of the formula (IX) per mole of starting material of the formula (I-a) is reacted at −20 to 150° C., preferably at 0 to 70° C.

The process (E) is preferably carried out in the presence of a diluent.

Suitable diluents are all inert polar organic solvents such as ethers, amides, ketones, carboxylic esters, nitrites, sulphones, sulphoxides or halogenated hydrocarbons such as methylene chloride.

Preference is given to using dimethyl sulphoxide, tetrahydrofuran, dimethylformamide, ethyl acetate, methylene chloride.

If, in a preferred embodiment, the enolate salt of the compounds of the formula (I-a) is prepared by addition of strong deprotonating agents (such as, for example, sodium hydride or potassium tert-butoxide), the addition of acid binders can be dispensed with.

If acid binders are used, then customary inorganic or organic bases are suitable, examples being sodium hydroxide, sodium carbonate, potassium carbonate, pyridine and triethylamine.

The reaction can be carried out under atmospheric pressure or under elevated pressure and is preferably carried out under atmospheric pressure. Work-up is carried out by customary methods.

The process (F) according to the invention is characterized in that compounds of the formula (I-a) are in each case reacted with phosphorus compounds of the formula (VIII), if appropriate in the presence of a diluent and if appropriate in the presence of an acid binder.

In the preparation process (F), 1 to 2, preferably 1 to 1.3, mol of the phosphorus compound of the formula (VIII) are reacted per mole of the compounds of the formula (I-a) at temperatures between 40° C. and 150° C., preferably between −10 and 110° C., in order to obtain compounds of the formula (I-e).

The process (F) is preferably carried out in the presence of a diluent.

Suitable diluents are all inert, polar organic solvents such as ethers, carboxylic esters, halogenated hydrocarbons, ketones, amides, nitrites, sulphones, sulphoxides, etc.

Preference is given to using acetonitrile, dimethyl sulphoxide, tetrahydrofuran, dimethylformamide, methylene chloride.

Acid binders which are added, if appropriate, are customary inorganic or organic bases, such as hydroxides, carbonates or amines. Examples include sodium hydroxide, sodium carbonate, potassium carbonate, pyridine and triethylamine.

The reaction can be carried out under atmospheric pressure or under elevated pressure and is preferably carried out under atmospheric pressure. Work-up is carried out according to customary methods of organic chemistry. The end products are preferably purified by crystallization, chromatographic purification or by so-called "incipient distillation", i.e. removal of the volatile components under reduced pressure.

The process (G) is characterized in that compounds of the formula (I-a) are in each case reacted with metal hydroxides or metal alkoxides of the formula (IX) or amines of the formula (X), if appropriate in the presence of a diluent.

Diluents which are preferred for use in the process (G) according to the invention are ethers such as tetrahydrofuran, dioxane, diethyl ether, or else alcohols such as methanol, ethanol, isopropanol, but also water. The process (G) according to the invention is generally carried out under atmospheric pressure. The reaction temperature is generally between −20° C. and 100° C., preferably between 0° C. and 50° C.

The process (H) according to the invention is characterized in that compounds of the formula (I-a) are in each case reacted with (Hα) compounds of the formula (XI), if appropriate in the presence of a diluent and if appropriate in the presence of a catalyst, or (Hβ) with compounds of the formula (XII), if appropriate in the presence of a diluent and if appropriate in the presence of an acid binder.

In the preparation process (Hα), approximately 1 mol of isocyanate of the formula (XI) is reacted per mole of starting material of the formula (I-a) at 0 to 100° C., preferably at 20 to 50° C.

The process (Hα) is preferably carried out in the presence of a diluent.

Suitable diluents are all inert organic solvents, such as aromatic hydrocarbons, halogenated hydrocarbons, ethers, amides, nitrites, sulphones or sulphoxides.

If appropriate, catalysts may be added to accelerate the reaction. Catalysts which can be employed very advantageously are organotin compounds, such as, for example, dibutyltin dilaurate.

The process is preferably carried out under atmospheric pressure.

In the preparation process (Hβ), approximately 1 mol of carbamoyl chloride of the formula (XIII) is reacted per mole of starting material of the formula (I-a) at 0 to 150° C., preferably at 20 to 70° C.

Diluents which may be added, if appropriate, are all inert polar organic solvents such as ethers, carboxylic esters, nitriles, ketones, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compounds of the formula (I-a) is prepared by addition of strong deprotonating agents (such as, for example, sodium hydride or potassium tert-butoxide), the addition of acid binders can be dispensed with.

If acid binders are employed, then customary inorganic or organic bases are suitable, examples including sodium hydroxide, sodium carbonate, potassium carbonate, triethylamine or pyridine.

The reaction can be carried out under atmospheric pressure or under elevated pressure and is preferably carried out under atmospheric pressure. Work-up is carried out by customary methods.

The active compounds are suitable for controlling animal pests, preferably arthropods and nematodes, in particular insects and arachnids, which are encountered in agriculture, in forests, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculate.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Frankliniella occidentalis, Hercinothrips femoralis, Thrips palmi,* and *Thrips tabaci. From the order of the Heteroptera, for example, Eurygaster spp., Dysdercus intermeditis, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasea spp., *Euscelis bilobatus, Nephotettix cincticeps, Lecanium comi, Saissetia oleac, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiclla, Bupalus piniarius, Cheimatobia brumata, Lithocolletis blancardella, Hyponomeuta padella, Plutella maculipemnnis, Malacosoma neustria, Euproctis chrysorrhoea,* Lymanitria spp. *Bucculatrix thurberiella, Phyllocnistis citrella,* Agrotis spp., Euxoa spp. Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dennestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon solsti tialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Liriomyza spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Omithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention have high insecticidal and acaricidal activity after foliar and soil application.

They can be employed particularly successfully against insects which are harmful to plants, such as, for example, against the larvae of the mustard beetle (*Phaedon cochleariae*), against the larvae of the rice green leafhopper (*Nephotettix cincticeps*) and against the larvae of the green peach aphid (*Myzus persicae*).

The active compounds according to the invention can furthermore be used as defoliants, desiccants, haulm killers and, especially, as weed-killers. By weeds, in the broadest sense, there are to be understood all plants which grow in locations where they are undesired. Whether the substances according to the invention act as total or selective herbicides depends essentially on the amount used.

The dosages of the active compounds according to the invention necessary for controlling weeds are between 0.001 and 10 kg/ha, preferably between 0.005 and 5 kg/ha.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Cardutus, Sonchus, Solanum, Rorippa, Rotola, Lindemia, Lamium, Veronica, Abutilon, Emex, Datura, Viola, Galeopsis, Papaver, Centaurca, Trifolium, Ranunculus and Taraxxacum.

Dicotyledonous crops of the genera: Gossypium, Glycine, Beta, Daucus, Phaseolus, Pisum, Solanum, Linum, pomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total controlling of weeds, for example on industrial terrain and rail tracks, and on paths and squares with or without tree plantings. Equally, the compounds can be employed for controlling weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hop fields, on ornamental and sports lawns and meadow areas and for the selective controlling of weeds in annual cultures.

The active compounds according to the invention are particularly suitable for selectively controlling monocotyledonous weeds in dicotyledonous crops by the pre- and post-emergence method. For example, they can he employed very successfully for controlling harmful grasses in cotton or sugar beet.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water, it is also possible to employ, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobeizenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as, acetone, methyl ethyl ketone, methyl isobutyl ketone or cyclohexanone, strongly polar solvents, such as dimethylformamide and dimethyl sulphoxide, and also water.

As solid carriers there are suitable:
for example, ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example, crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifying and/or foam-forming agents there are suitable: for example, non-ionic and anionic emulsifiers, such as polyoxyethylene fatty acid esters, polyoxyethylene fatty alcohol ethers, for example alkylaryl polyglycol ethers, alkyl sulphonates, alkyl sulphates, aryl sulphonates and also protein hydrolysates; as dispersing agents there are suitable: for example, lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%, and additionally preferably extenders and/or surfactants.

The active compound according to the invention can be present in its commercially available formulations and in the use forms prepared from these formulations as a mixture with other active compounds, such as insecticides, baits, sterilizing agents, acaricides, nematicides, fungicides, growth-regulating substances or herbicides. The insecticides include, for example, phosphoric acid esters, carbamates, carboxylic acid esters, chlorinated hydrocarbons, phenylureas, substances produced by microorganisms, and the like.

Particularly favourable mixing partners are, for example, the following:

Fungicides 2-aminobutane; 2-anilino-4-methyl-6-cyclopropyl-pyrimidine; 2',6'dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxy-phenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides bronopol, dichlorophen, nitrapyrin, nickel dimethyldithiocarbamate, kasugamycin, octhilinon, furancarboxylic acid, oxytetracyclin, probenazol, streptomycin, tecloftalam, copper sulphate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenlprox, ethoproplios, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, primiphos A, profenofos, promecarb, propaphos, propoxur, prothiofos, prothoate, pymetrozin, pyrachliophos, pyridaphenthion, pyresmethrin, pyrethrumn, pyridaben, pyrimidifen, pyriproxifen, quinalphos, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides for example anilides, such as, for example, diflufenican and propanil; arylcarboxylic acids such as, for example, dichloropicolinic acid, dicamba and picloram; aryloxyalkanoic acids, such as, for example, 2,4 D, 2,4 DB, 2,4 DP, fluroxypyr, MCPA, MCPP and triclopyr; aryloxy-phenoxyalkanoic acid esters, such as, for example, diclofop-methyl, fenoxaprop-ethyl, fluazifop-butyl, haloxyfop-methyl and quizalofop-ethyl; azinones, such as, for example, chloridazon and norflurazon; carbamates, such as, for example, chlorpropham, desmedipham, phenmedipham and propham; chloroacetanilides, such as, for example, alachlor, acetochlor, butachlor, metazachlor, metolachlor, pretilachlor and propachlor; dinitroanilines, such as, for example, oryzalin, pendimethalin and trifluralin; diphenyl ethers, such as, for example, acifluorfen, bifenox, fluoroglycofen, fomesafen, halosafen, lactofen and oxyfluorfen; ureas, such as, for example, chlortoluron, diuron, fluometuron, isoproturon, linuron and methabenzthiazuron; hydroxylamines, such as, for example, alloxydim, clethodim, cycloxydim, sethoxydim and tralkoxydim; imidazolinones, such as, for example, imazethapyr, imazamethabenz, imazapyr and imazaquin; nitriles, such as, for example, bromoxynil, dichlobenil and ioxynil; oxyacetamides, such as, for example, mefenacet; sulfonylureas, such as, for example, amidosulfuron, bensulfiron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulftiron and tribenuron-methyl; thiocarbamates, such as, for example, butylate, cycloate, di-allate, EPTC, esprocarb, molinate, prosulfocarb, thiobencarb and tri-allate; triazines, such as, for example, atrazine, cyanazine, simazine, simetryn, terbutryn and terbutylazine; triazinones, such as, for example, hexazinone, metamitron and metribuzin; others, such as, for example, aminotriazole, benfuresate, bentazone, cinrethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms, prepared from these formulations, as a mixture with synergists. Synergists are compounds which increase the action of the active compounds without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are used in a customary manner appropriate for the use forms.

When used against hygiene pests and pests of stored products, the active compound has outstanding residual action on wood and clay and a stability to alkali on limed substrates.

The active compounds according to the invention have an action not only against plant and hygiene pests and pests of stored products, but also in the veterinary medicine sector against animal parasites (ectoparasites), such as hard ticks, soft ticks, mange mites, harvest mites, flies (biting and licking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Wemeckiella spp., Lepikentron spp., Damalina spp., Trichodectes spp., Felicola spp.

From the order of the Diptera and the suborders Nematocerina and Brachycerilia, for example, Aedes spp., Anopheles spp., Culex spp., Simulium spp., Eusimulium spp. Phlebotomus spp., Lutzomyia spp., Culicoides spp., Chrysops spp., Hybomitra spp. Atylotus spp., Tabanus spp., Haematopota spp., Philipomyia spp., Braula spp. Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Stemostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pteroliclius spp., Psoroptes spp., Chorioptes spp., Otodectes spp., Sarcoptes spp., Notoedres spp., Knemidocoptes spp., Cytodites spp. and Laminosioptes spp.

The active compounds of the formula (I) according to the invention are also suitable for controlling arthropods which infest agricultural productive livestock such as, for example, cattle, sheep, goats, horses, pigs, donkeys, camels, buffalo, rabbits, chickens, turkeys, ducks, geese and bees, other pets, such as, for example, dogs, cats, cage birds and aquarium fish, and also so-called test animals, such as, for example, hamsters, guinea pigs, rats and mice. By controlling these arthropods, mortality and reductions in productivity (for meat, milk, wool, hides, eggs, honey, etc.) should be diminished, so that more economic and simpler animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injections (intramuscular, subcutaneous, intravenous, intraperitoneal, etc.), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices, etc.

When used for livestock, poultry, pets and the like, the active compounds of the formula (I) can be used as formulations (for example powders, emulsions, flowables) which comprise the active compounds in an amount of 1 to 80% by weight, directly or after 100 to 10,000-fold dilution, or they can be used as a chemical bath.

It has furthermore been found that the compounds of the formula (I) according to the invention display a high insecticidal action against insects which destroy industrial materials.

The following insects may be mentioned as examples and preferred—but without being limiting:

Beetles, such as *Hylotrupes bajulus, Chlorophoris pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis*, Xyleborus spec., Tryptodendron spec, *Apate monachus, Bostrychus capucins, Heterobostrychus brunneus*, Sinoxylon spec. and *Dinoderus minutus*.

Hymenopterons, such as *Sirex juvencus, Urocerus gigas, Urocemis gigas taignus* and *Urocerus augur*.

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*.

Bristletails, such as *Lepisma saccharina*.

Industrial materials in the present connection are to be understood as meaning non-living materials, such as, preferably, plastics, adhesives, sizes, papers and cards, leather, wood and processed wood products, and lacquers and paints.

Materials to be protected from insect damage which are quite particularly preferred are wood and processed wood products.

Wood and processed wood products which can be protected by the agents according to the invention or mixtures comprising these are to be understood as meaning, for example: building timber, wooden beams, railway sleepers, bridge components, boat gangplanks, wooden vehicles, crates, pallets, containers, telegraph poles, wood lagging, wooden windows and doors, plywood, chipboards, joinery or wood products used quite generally in house construction or building joinery.

The active compounds can be used as such or in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, water repellant, optionally siccatives and UV stabilizers, and if appropriate dyestuffs and pigments, and also other processing auxiliaries.

The insecticidal compositions or concentrates used for preservation of wood and derived timber products comprise the active compound according to the invention in a concentration of 0.0001 to 95% by weight, in particular 0.001 to 60% by weight.

The amount of composition or concentrate employed depends on the nature and the occurrence of the insects and on the medium. The optimum amount employed for the use can in each case be determined by a series of tests. In general, however, it is sufficient to employ 0.0001 to 20% by weight, preferably 0.001 to 10% by weight, of the active compound based on the material to be preserved.

The solvent and/or diluent used is an organochemical solvent or solvent mixture and/or an oily or oil-like organochemical solvent or solvent mixture of low volatility and/or a polar organochemical solvent or solvent mixture and/or water and, if appropriate, an emulsifier and/or wetting agent.

The organochemical solvents employed are preferably oily or oil-like solvents having an evaporation number above 35 and a flash point above 30° C., preferably above 45° C. Corresponding mineral oils or aromatic fractions thereof or solvent mixtures containing mineral oil, preferably white spirit, petroleum and/or alkylbenzene, are used as such water-insoluble, oily and oil-like solvents of low volatility.

Mineral oils having a boiling range from 170 to 220° C., white spirit having a boiling range from 170 to 220° C., spindle oil having a boiling range from 250 to 350° C., petroleum or aromatics having a boiling range from 160 to 280° C., terpentine oil and the like are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably monochloronaphthalene, are employed.

The organic oily or oil-like solvents of tow volatility having an evaporation number above 35 and a flash point above 30° C., preferably above 45° C., can be replaced in part by organochemical solvents of high or medium volatility, provided that the solvent mixture likewise has an evaporation number above 35 and a flash point above 30° C., preferably above 45° C., and that the insecticide/fungicide mixture is soluble or can be emulsified in this solvent mixture.

According to a preferred embodiment, some of the organochemical solvent or solvent mixture is replaced by an aliphatic polar organochemical solvent or solvent mixture. Aliphatic organochemical solvents containing hydroxyl and/or ester and/or ether groups, such as, for example, glycol ethers, esters or the like, are preferably used.

Organochemical binders which are used within the context of the present invention are the synthetic resins and/or binding drying oils which are water-dilutable and/or soluble or dispersible or emulsifiable in the organochemical solvents employed and are known per se, in particular binders consisting of or comprising an acrylate resin, a vinyl resin. for example polyvinyl acetate, polyester resin, polycondensation or polyaddition resin, polyurethane resin, alkyd resin or modified alkyd resin, phenolic resin, hydrocarbon resin, such as indene-coumarone resin or silicone resin, drying plant and/or drying oils and/or binders which dry by physical, means and are based on a naturally occurring and/or synthetic resin.

The synthetic resin used as the binder can be employed in the form of an emulsion, dispersion or solution. Bitumen or bituminous substances can also be used as binders in an amount of up to 10% by weight. In addition, dyestuffs, pigments, water-repellant agents, odour correctants and inhibitors or corrosion prevention agents and the like which are known per se can be employed.

Preferably, according to the invention, the composition or concentrate comprises at least one alkyd resin or modified alkyd resin and/or one drying plant oil as an organochemical binder. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl)adipate, stearates, such as butyl stearate or amyl stearate, oleates, such as butyl oleate, glycerol ethers or higher molecular weight glycol ethers, glycerol esters and ptoluenesulphonic acid esters.

Fixing agents are based chemically on polyvinyl alkyl ethers, such as, for example, polyvinyl methyl ether, or ketones, such as benzophenone or ethylenebenzophenone.

Water in particular is also a possible solvent or diluent, if appropriate mixed with one or more of the abovementioned organochemical solvents or diluents, emulsifiers and dispersing agents.

Particularly effective wood preservation is achieved by impregnation processes on a large industrial scale, for example vacuum, double vacuum or pressure processes.

If appropriate, the ready-to-use compositions can also comprise other insecticides, and if appropriate also one or more fungicides.

Possible additional admixing partners are, preferably, the insecticides and fungicides mentioned in WO 94/29 268. The compounds mentioned in this document are an express constituent of the present application.

Especially preferred admixing partners can be insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo-2-propinyl butylcarbamate, N-octylisothiazolin-3-one and 4,5-dichloro-N-octylisothiazolin-3-one.

The preparation and the use of the active compounds according to the invention can be seen from the following examples.

EXAMPLE (I-a-1)

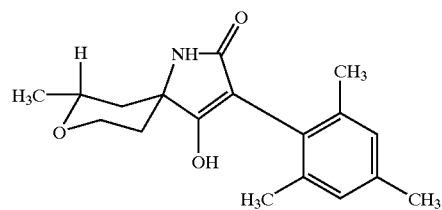

At reflux temperature, 24.8 g of the compound of Example (II-2) in 150 ml of anhydrous toluene are added dropwise to 18.4 g (0.16 mol) of potassium tert-butoxide in 63 ml of anhydrous tetrahydrofuran (THF), and the mixture is stirred at reflux for another 1.5 hours. 240 ml of water are then added, the phases are separated and the toluene phase is extracted with water. The combined aqueous phases are washed with toluene and, at 10 to 20° C., acidified with approximately 26 ml of conc. hydrochloric acid. The precipitated solid is filtered off with suction, washed and dried. For purification, the product is stirred in a mixture of methyl tert-butyl ether (MTB ether) and n-hexane.

Yield 15.6 g (69% of theory), m.p.: >220° C.

Similar to this method, and/or according to the general preparation procedures, the following compounds of the formula (I-a) are obtained:

TABLE 2

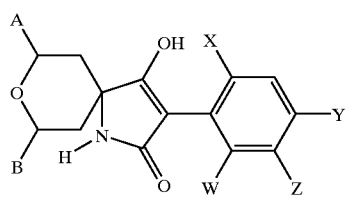

(I-a)

| Ex. No. | W | X | Y | Z | A | B | m.p. ° C. | isomer |
|---|---|---|---|---|---|---|---|---|
| I-a-2 | CH₃ | CH₃ | CH₃ | H | CH₃ | H | 195 | α |
| I-a-3 | H | CH₃ | CH₃ | H | CH₃ | H | 164 | α |
| I-a-4 | H | CH₃ | CH₃ | H | CH₃ | H | 196 | β |
| I-a-5 | C₂H₅ | C₂H₅ | CN | H | CH₃ | H | 242 | β |
| I-a-6 | H | Cl | Cl | H | CH₃ | H | >220 | β |
| I-a-7 | H | Cl | CH₃ | H | CH₃ | H | 194 | β |
| I-a-8 | Cl | CH₃ | Cl | H | CH₃ | H | >220 | β |
| I-a-9 | Cl | Cl | CH₃ | H | CH₃ | H | 211 | β |
| I-a-10 | CH₃ | CH₃ | CH₃ | CH₃ | CH₃ | H | >220 | β |
| I-a-11 | H | CH₃ | Cl | H | CH₃ | H | >220 | β |
| I-a-12 | CH₃ | CH₃ | CN | H | CH₃ | H | >220 | β |
| I-a-13 | CH₃ | CH₃ | H | Cl | CH₃ | H | 210 | β |
| I-a-14 | H | CH₃ | CH₃ | CH₃ | CH₃ | H | >220 | β |
| I-a-15 | H | Cl | Br | H | CH₃ | H | >220 | β |
| I-a-16 | CH₃ | CH₃ | Cl | H | CH₃ | H | 211 | β |
| I-a-17 | CH₃ | CN | CH₃ | H | CH₃ | H | >220 | β |
| I-a-18 | CH₃ | CH₃ | Br | H | CH₃ | H | >220 | β |
| I-a-19 | Br | CH₃ | Cl | H | CH₃ | H | 210 | β |
| I-a-20 | H | CH₃ | H | CH₃ | CH₃ | H | >220 | β |
| I-a-21 | Br | Br | C₂H₅ | H | CH₃ | H | >220 | β |
| I-a-22 | H | Cl | C₂H₅ | H | CH₃ | H | >220 | β |
| I-a-23 | CH₃ | CH₃ | CH₃ | H | CH₃ | CH₃ | >220 | α |
| I-a-24 | H | CH₃ | CH₃ | H | CH₃ | CH₃ | >220 | α |
| I-a-25 | H | Cl | Cl | CH₃ | CH₃ | H | >240 | β |
| I-a-26 | H | Cl | CH₃ | Cl | CH₃ | H | >236 | β |
| I-a-27 | H | CH₃ | Cl | CH₃ | CH₃ | H | >227 | β |
| I-a-28 | H | Br | CH₃ | Br | CH₃ | H | >240 | β |
| I-a-29 | H | CH₃ | Cl | Cl | CH₃ | H | 206 | β |

TABLE 2-continued

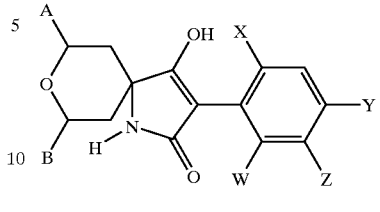

(I-a)

| Ex. No. | W | X | Y | Z | A | B | m.p. ° C. | isomer |
|---|---|---|---|---|---|---|---|---|
| I-a-30 | Br | Br | i-C₃H₇ | H | CH₃ | H | 233 | β |
| I-a-31 | Cl | Cl | Cl | H | CH₃ | H | >234 | β |

EXAMPLE (I-b-1)

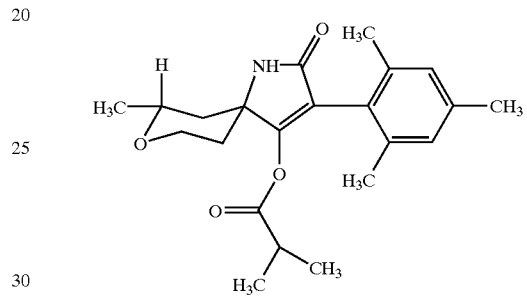

2.52 mol (18 mmol) of triethylamine are added to 3.62 g of the compound of 5 Example (I-a-1) in 70 ml of anhydrous methylene chloride. At 0 to 10° C., 1.9 ml (18 mmol) of isobutyryl chloride in 5 ml of anhydrous methylene chloride are added to this mixture, and stirring is continued at room temperature until the reaction has ended. The mixture is then washed twice with 50 ml of 0.5 N NaOH each time, dried and concentrated. The residue is recrystallized from MTB ether/n-hexane.

Yield 1.6 g (35% of theory), m.p.: 209° C.

Similar to this method, and/or according to the general preparation procedures, the following compounds of the formula (I-b) are obtained:

TABLE 3

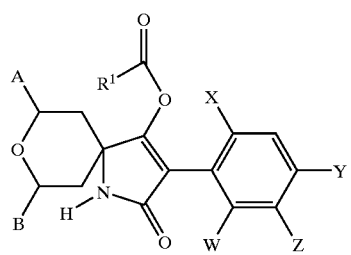

(I-b)

| Ex. No. | W | X | Y | Z | A | B | R¹ | m.p. ° C. | isomer |
|---|---|---|---|---|---|---|---|---|---|
| I-b-2 | CH₃ | CH₃ | CH₃ | H | CH₃ | H | CH₃ | 176 | α |
| I-b-3 | CH₃ | CH₃ | CH₃ | H | CH₃ | H | i-C₃H₇ | 187 | α |
| I-b-4 | H | CH₃ | CH₃ | H | CH₃ | H | i-C₃H₇ | | α[1] |
| I-b-5 | CH₃ | CH₃ | CH₃ | H | CH₃ | H | CH₃ | 187 | β |
| I-b-6 | H | CH₃ | CH₃ | H | CH₃ | H | CH₃ | 181 | β |

TABLE 3-continued

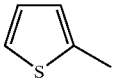

(I-b)

| Ex. No. | W | X | Y | Z | A | B | R¹ | m.p. °C. | isomer |
|---|---|---|---|---|---|---|---|---|---|
| I-b-7 | H | $CH_3$ | $CH_3$ | H | $CH_3$ | H | $i\text{-}C_3H_7$ | 211 | β |
| I-b-8 | H | Cl | $CH_3$ | H | $CH_3$ | H | $i\text{-}C_3H_7$ | 155 | β |
| I-b-9 | Cl | Cl | $CH_3$ | H | $CH_3$ | H | $i\text{-}C_3H_7$ | 178 | β |
| I-b-10 | $CH_3$ | Cl | Cl | H | $CH_3$ | H | $i\text{-}C_3H_7$ | 204 | β |
| I-b-11 | $CH_3$ | $CH_3$ | $CH_3$ | $CH_3$ | $CH_3$ | H | $i\text{-}C_3H_7$ | >220 | β |
| I-b-12 | $CH_3$ | $CH_3$ | CN | H | $CH_3$ | H | $i\text{-}C_3H_7$ | 214 | β |
| I-b-13 | $CH_3$ | $CH_3$ | CN | H | $CH_3$ | H | $t\text{-}C_4H_9\text{---}CH_2$ | >220 | β |
| I-b-14 | H | $CH_3$ | $CH_3$ | $CH_3$ | $CH_3$ | H | $i\text{-}C_3H_7$ | 210 | β |
| I-b-15 | H | Cl | Br | H | $CH_3$ | H | $i\text{-}C_3H_7$ | 170 | β |
| I-b-16 | H | Cl | Br | H | $CH_3$ | H | $t\text{-}C_4H_9\text{---}CH_2$ | 194 | β |
| I-b-17 | H | $CH_3$ | Cl | H | $CH_3$ | H | $i\text{-}C_3H_7$ | 178 | β |
| I-b-18 | $CH_3$ | CN | $CH_3$ | H | $CH_3$ | H | $i\text{-}C_3H_7$ | 214 | β |
| I-b-19 | $CH_3$ | CN | $CH_3$ | H | $CH_3$ | H | $t\text{-}C_4H_9\text{---}CH_2$ | >200 | β |
| I-b-20 | $CH_3$ | $CH_3$ | Br | H | $CH_3$ | H | $i\text{-}C_3H_7$ | >220 | β |
| I-b-21 | $CH_3$ | $CH_3$ | Br | H | $CH_3$ | H | $t\text{-}C_4H_9\text{---}CH_2$ | >220 | β |
| I-b-22 | H | Cl | $C_2H_5$ | H | $CH_3$ | H | $i\text{-}C_3H_7$ | 179 | β |
| I-b-23 | H | Cl | $C_2H_5$ | H | $CH_3$ | H | 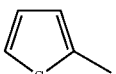 | 152 | β |
| I-b-24 | H | $CH_3$ | $CH_3$ | $CH_3$ | $CH_3$ | H | 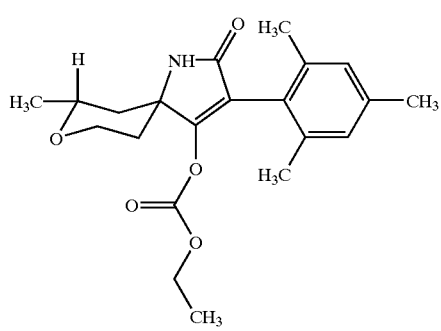 | 170 | β |
| I-b-25 | $CH_3$ | $CH_3$ | Cl | H | $CH_3$ | H | $i\text{-}C_3H_7$ | 160 | β |
| I-b-26 | $CH_3$ | $CH_3$ | Cl | H | $CH_3$ | H | $s\text{-}C_4H_9$ | 200 | β |
| I-b-27 | H | $CH_3$ | H | $CH_3$ | $CH_3$ | H | $i\text{-}C_3H_7$ | 193 | β |
| I-b-28 | $CH_3$ | $CH_3$ | $CH_3$ | H | $CH_3$ | $CH_3$ | $i\text{-}C_3H_7$ | 191 | α |
| I-b-29 | H | Cl | $CH_3$ | Cl | $CH_3$ | H | $i\text{-}C_3H_7$ | 231 | β |
| I-b-30 | H | $CH_3$ | Cl | $CH_3$ | $CH_3$ | H | $i\text{-}C_3H_7$ | 210 | β |
| I-b-31 | H | Br | $CH_3$ | Br | $CH_3$ | H | $i\text{-}C_3H_7$ | 214–216 | β |
| I-b-32 | H | Cl | Cl | $CH_3$ | $CH_3$ | H | $i\text{-}C_3H_7$ | 202–205 | β |
| I-b-33 | Br | Br | $C_2H_5$ | H | $CH_3$ | H | $i\text{-}C_3H_7$ | 217 | β |
| I-b-34 | $CH_3$ | $CH_3$ | Cl | H | $CH_3$ | H | $(CH_3)_2C\text{=}CH$ | >248 | β |
| I-b-35 | Cl | Cl | Cl | H | $CH_3$ | H | $i\text{-}C_3H_7$ | 207 | β |
| I-b-36 | Br | Br | $i\text{-}C_3H_7$ | H | $CH_3$ | H | $i\text{-}C_3H_7$ | 213 | β |

¹⁾¹H-NMR (200 MHz, CDCl₃): δ = 1.0–1.05 (4s, 6H, CH(C$\underline{H}_3$)₂), 2.25, 2.28 (2s, 6H, ArC$\underline{H}_3$).

EXAMPLE (I-c-1)

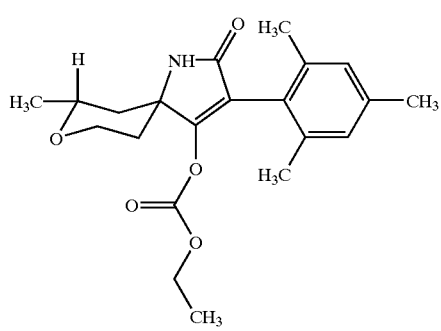

At 0 to 10° C., 1.2 ml (12 mmol) of ethyl chloroformate in 5 ml of anhydrous methylene chloride are added dropwise to 3.62 g of the compound of Example (I-a-1) and 1.7 ml (12 mmol) of triethylamine in 70 ml of anhydrous methylene chloride, and the mixture is stirred at room temperature until the reaction has ended. The mixture is then washed two times with 50 ml of 0.5 N NaOH each time, dried and concentrated and the residue is recrystallized from MTB ether/n-hexane.

Yield 2.70 g (60% of theory), m.p.: 217° C.

Similar to this method, and/or according to the general preparation procedures, the following compounds of the formula (I-c) are obtained:

TABLE 4

(I-c)

[Structure of compound I-c shown]

| Ex. No. | W | X | Y | Z | A | B | M | R² | m.p. °C | isomer |
|---|---|---|---|---|---|---|---|---|---|---|
| I-c-2 | CH₃ | CH₃ | CH₃ | H | CH₃ | H | O | C₂H₅ | 201 | α |
| I-c-3 | H | CH₃ | CH₃ | H | CH₃ | H | O | C₂H₅ | 122 | α |
| I-c-4 | H | CH₃ | CH₃ | H | CH₃ | H | O | C₂H₅ | 197 | β |
| I-c-5 | CH₃ | CH₃ | CH₃ | CH₃ | CH₃ | H | O | C₂H₅ | 211 | β |
| I-c-6 | CH₃ | CH₃ | CN | H | CH₃ | H | O | C₂H₅ | 229 | β |
| I-c-7 | H | CH₃ | CH₃ | CH₃ | CH₃ | H | O | C₂H₅ | 171 | β |
| I-c-8 | H | Cl | Br | H | CH₃ | H | O | C₂H₅ | 201 | β |
| I-c-9 | H | CH₃ | Cl | H | CH₃ | H | O | C₂H₅ | 198 | β |
| I-c-10 | CH₃ | CN | CH₃ | H | CH₃ | H | O | C₂H₅ | 197 | β |
| I-c-11 | CH₃ | CH₃ | Br | H | CH₃ | H | O | C₂H₅ | >220 | β |
| I-c-12 | H | Cl | Cl | H | CH₃ | H | O | C₂H₅ | 171 | β |
| I-c-13 | H | Cl | C₂H₅ | H | CH₃ | H | O | C₂H₅ | 196 | β |
| I-c-14 | CH₃ | CH₃ | Cl | H | CH₃ | H | O | C₂H₅ | 205 | β |
| I-c-15 | H | CH₃ | H | CH₃ | CH₃ | H | O | C₂H₅ | 185 | β |
| I-c-16 | CH₃ | CH₃ | CH₃ | H | CH₃ | CH₃ | O | C₂H₅ | 218 | α |
| I-c-17 | H | Cl | CH₃ | Cl | CH₃ | H | O | C₂H₅ | 222 | β |
| I-c-18 | H | CH₃ | Cl | CH₃ | CH₃ | H | O | C₂H₅ | 206 | β |
| I-c-19 | H | Br | CH₃ | CH₃ | CH₃ | H | O | C₂H₅ | 159–160 | β |
| I-c-20 | Br | C₂H₅ | Br | H | CH₃ | H | O | C₂H₅ |  | β |

EXAMPLE (II-1)

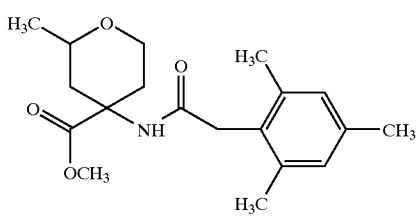

At 30 to 40° C., 27.8 g of the compound of Example (XXIII-1) in 180 ml of methylene chloride are added dropwise to 45.4 g of concentrated sulphuric acid, and the mixture is stirred for another 2 hours at 30 to 40° C. 64 ml of anhydrous methanol are then added dropwise, and the mixture is stirred for another 6 hours at 40 to 70° C. The mixture is then poured onto 0.46 kg of ice and extracted with methylene chloride, and the organic phase is washed with aqueous NaHCO₃ solution, dried and concentrated. The residue is recrystallized from MTB ether/n-hexane.

Yield 19.80 g (64% of theory), m.p.: 101° C.

EXAMPLE (II-2)

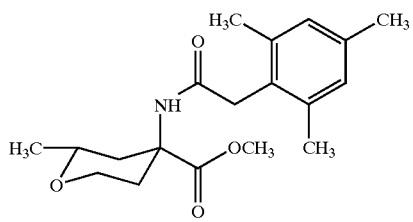

At 0 to 10° C., 19.6 g of mesityleneacetyl chloride in 20 ml of anhydrous THF are added dropwise to 20.98 g of the compound of Example (XIII-1) and 30.8 ml (0.22 mol) of triethylamine in 200 ml of anhydrous THF, and the mixture is stirred at room temperature until the reaction has ended. The mixture is filtered off with suction, the filter cake is rinsed and the filtrate is concentrated. The residue is taken up in methylene chloride, washed with 200 ml 1 N HCl, dried and concentrated. Silica gel column chromatography using cyclohexane/ethyl acetate 2/1 gives 24.0 g (72% of theory). ¹H NMR (200 MHz, CDCl₃): δ=1.12 (d, 3H, CH—$\underline{CH_3}$), 3.51 (α), 3.6 (β) (2s, 2H, $\underline{CH_2}$, CONH, β/α approximately 3:1), 3.71, 3.75 (α/β) (2s, 3H, CO₂CH₃, (β/α 3:1), 6.90 (α), 6.92 (β) (2s, 2H, ArH).

Similar to this method, and/or according to the general preparation procedures, the following compounds of the formula (II) are obtained:

TABLE 5

(II)

| Ex. No. | W | X | Y | Z | A | B | R⁸ | m.p. °C. | isomer |
|---|---|---|---|---|---|---|---|---|---|
| II-3 | H | $CH_3$ | $CH_3$ | H | $CH_3$ | H | $CH_3$ | 71 | α |
| II-4 | H | $CH_3$ | $CH_3$ | H | $CH_3$ | H | $CH_3$ |  | β[1] |
| II-5 | $CH_3$ | $CH_3$ | $CH_3$ | H | $CH_3$ | $CH_3$ | $CH_3$ | 106 | α |
| II-6 | H | $CH_3$ | $CH_3$ | H | $CH_3$ | $CH_3$ | $CH_3$ | 96 | α |
| II-7 | $C_2H_5$ | $C_2H_5$ | CN | H | $CH_3$ | H | $CH_3$ |  | β[2] |
| II-8 | H | Cl | Cl | H | $CH_3$ | H | $CH_3$ |  | β[3] |
| II-9 | H | Cl | $CH_3$ | H | $CH_3$ | H | $CH_3$ |  | β[4] |
| II-10 | $CH_3$ | Cl | Cl | H | $CH_3$ | H | $CH_3$ | 125–127 | β |
| II-11 | Cl | Cl | $CH_3$ | H | $CH_3$ | H | $CH_3$ | 171 | β |
| II-12 | H | Cl | $C_2H_5$ | H | $CH_3$ | H | $CH_3$ |  | β[5] |
| II-13 | $CH_3$ | $CH_3$ | CN | H | $CH_3$ | H | $CH_3$ | 111 | β |
| II-14 | $CH_3$ | $CH_3$ | $CH_3$ | $CH_3$ | $CH_3$ | H | $CH_3$ | 150 | β |
| II-15 | H | $CH_3$ | $CH_3$ | $CH_3$ | $CH_3$ | H | $CH_3$ | 122 | β |
| II-16 | $CH_3$ | $CH_3$ | H | Cl | $CH_3$ | H | $CH_3$ | 159 | β |
| II-17 | H | $CH_3$ | Cl | H | $CH_3$ | H | $CH_3$ | 160 | β |
| II-18 | H | $CH_3$ | $CH_3$ | $CH_3$ | $CH_3$ | H | $CH_3$ | 141 | β |
| II-19 | H | Cl | Br | H | $CH_3$ | H | $CH_3$ | 134 | β |
| II-20 | $CH_3$ | Cl | Br | H | $CH_3$ | H | $CH_3$ | 164 | β |
| II-21 | $CH_3$ | $CH_3$ | Cl | H | $CH_3$ | H | $CH_3$ | 118 | β |
| II-22 | $CH_3$ | CN | $CH_3$ | H | $CH_3$ | H | $CH_3$ | 135 | β |
| II-23 | $CH_3$ | $CH_3$ | Br | H | $CH_3$ | H | $CH_3$ | 156 | β |
| II-24 | $CH_3$ | Br | Cl | H | $CH_3$ | H | $CH_3$ | 150 | β |
| II-25 | H | $CH_3$ | H | $CH_3$ | $CH_3$ | H | $CH_3$ | 117 | β |
| II-26 | Br | Br | $C_2H_5$ | H | $CH_3$ | H | $CH_3$ | 141 | β |
| II-27 | Cl | Cl | Cl | H | $CH_3$ | H | $CH_3$ | 156 | β |
| II-28 | Br | Br | i-$C_3H_7$ | H | $CH_3$ | H | $CH_3$ | 126 | β |
| II-29 | H | Cl | Cl | $CH_3$ | $CH_3$ | H | $CH_3$ | 150–152 | β |
| II-30 | H | Cl | $CH_3$ | Cl | $CH_3$ | H | $CH_3$ | 118–120 | β |
| II-31 | H | $CH_3$ | Cl | $CH_3$ | $CH_3$ | H | $CH_3$ | 144–146 | β |
| II-32 | H | Br | $CH_3$ | Br | $CH_3$ | H | $CH_3$ | 138–140 | β |
| II-33 | H | $CH_3$ | Cl | Cl | $CH_3$ | H | $CH_3$ | 146 | β |

[1] $^1$H NMR (200 MHz, $CDCl_3$): 1.12 (d, 3H, CH$CH_3$), 2.24 (α), 2.28 (β), (2s, 3H, Ar-2-$CH_3$), 2.37 (s, 3H, Ar-4-$CH_3$), 3.49 (α), 3.55 (β), (2s, 2H, $CH_2$CONH), 3.62 (β), 3.65 (α), (2s, 3H, $CO_2CH_3$, α/β approximately 1:3)
[2] $^1$H NMR (400 MHz, $CDCl_3$): δ = 1.13 (α), 1.14 (β), (2d, 3H, CH$CH_3$); α/β approximately 1:3), 1.36 (t, 6H, ($CH_2$$CH_3$)$_2$), 2.70 (q, 4H, ($CH_2$—$CH_3$)$_2$), 7.40 (α), 7.42 (β), (2s, 2H, Ar—H, α/β approximately 1:3
[3] $^1$H NMR (400 MHz, $CDCl_3$): δ = 1.15, 1.16 (2d, 3H, CH$CH_3$), 3.67–3.71 (3s, 5H, $CH_2$CONH, $CO_2$$CH_3$), 7.21–7.32 (m, 2H, Ar$H$), 7.4–7.45 (m, 1H, ArH)
[4] $^1$H NMR (400 MHz, $CDCl_3$): δ = 1.14 (d, 3H, CH$CH_3$), 2.34 (s, 3H, Ar$CH_3$), 7.03–7.09 (m, 1H, Ar—H), 7.17–7.27 (m, 2H, Ar—H).
[5] $^1$H NMR (400 MHz, $CDCl_3$): δ = 1.14 (2d, 3H, CH$CH_3$), 1.23 (t, 3H, $CH_2$$CH_3$), 2.53 (q, 2H, $CH_2CH_3$), 7.08–7.12 (m, 1H, ArH), 7.25–7.29 (m, 2H, Ar—H).

EXAMPLE (XIII-1)

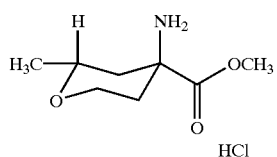

HCl

At 0 to 5° C., 73.2 ml (0.87 mol) of thionyl chloride are added dropwise to 92.3 g of the compound of Example (XVI-1) in 870 ml of anhydrous methanol, and the mixture is stirred at approximately 0° C. for 30 minutes and then at approximately 40° C. overnight. The mixture is filtered, the filtrate is concentrated and the residue is stirred with a little MTB ether, the mixture is filtered off with suction and the filter cake is rinsed and dried.

Yield 87.0 g (86% of theory), m.p.: >220° C.

EXAMPLE (XVI-1)

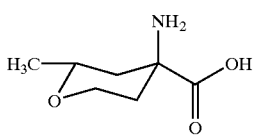

122.8 g of the compound of the example below and 130 g of NaOH in 2.5 l of water are heated in an autoclave at 195° C. for 2 hours, the pressure increasing to approximately 20 bar. The mixture is then concentrated to approximately ⅓ of its volume, concentrated HCl is added at 0 to 10° C. until the pH is 5 to 6, the mixture is concentrated, the residue is boiled with methanol, the mixture is filtered off with suction and the filtrate is concentrated.

Yield 92.3 g (86% of theory), m.p.: >220° C.

EXAMPLE: COMPOUND OF THE FORMULA

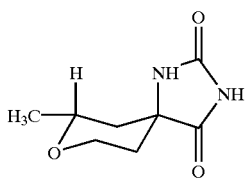

In an autoclave, a mixture comprising 76 g of 3-methyltetrahydropyran-4-one, 71.9 g (1.468 mol) of sodium cyanide, 96 g (1 mol) of ammonium carbonate, 1.32 l of concentrated ammonia solution and 1.32 l of ethanol is stirred at 120° C. for 3 hours, the internal pressure increasing to approximately 60 bar (prior to heating, ⅔ of the desired reaction pressure is applied). The mixture is concentrated, dried with toluene, boiled with methanol and filtered off with suction. The mother liquor is concentrated to 400 ml, and further solid components are precipitated by addition of MTB ether and are filtered off with suction. The mother liquor is concentrated. The combined residues are boiled in ethanol, the mixture is filtered off with suction (A). and the filtrate is concentrated (B). (A) and (B) are combined.

Yield 126.0 g (100% of theory).

EXAMPLE (XXIII-1)

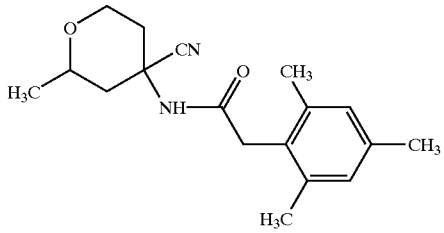

At 0 to 10° C., 21.6 g of mesitylene acetyl chloride in 20 ml of anhydrous THF are added dropwise to 15.6 g of the compound of Example (XXII-1) and 15.4 ml of triethylamine in 220 ml of anhydrous THF, and the mixture is stirred at room temperature until the reaction has ended. The mixture is stirred into 0.6 l of ice-water and 0.2 l of 1 N HCl and filtered off with suction, and the residue is taken up in methylene chloride. The solution is dried and concentrated and the residue is re-crystallized from MTB ether/n-hexane.

Yield 27.8 g (84% of theory), m.p.: 121° C.

Similar to this method, and/or according to the general preparation procedures, the following compounds of the formula (XXIII) are obtained:

TABLE 6

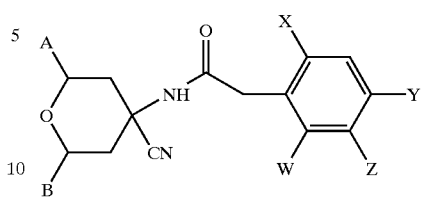

(XXIII)

| Ex. No. | W | X | Y | Z | A | B | m.p. ° C. |
|---|---|---|---|---|---|---|---|
| XXIII-2 | H | $CH_3$ | $CH_3$ | H | $CH_3$ | H | 112 |
| XXIII-3 | $CH_3$ | $CH_3$ | $CH_3$ | H | $CH_3$ | $CH_3$ | 127 |
| XXIII-4 | H | $CH_3$ | $CH_3$ | H | $CH_3$ | $CH_3$ | 118 |

EXAMPLE (XIV-1)

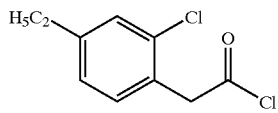

At 70° C., 99.3 g of 2-chloro-4-ethylphenylacetic acid and 109 ml (1.5 mol) of thionyl chloride are stirred until the evolution of gas has ended. Excess thionyl chloride is removed at 50° C. under reduced pressure. The residue is distilled.

Yield 99.10 g (91% of theory), b.p. 121° C./0–35 mbar.

EXAMPLE (XVII-1)

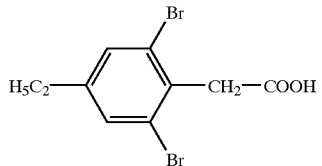

102 .5 g (16.9% strength, 0.05 mol) of the compound of Example (XVIII-1), 14.1 g of KOH, 17.8 ml of water and 35.5 ml of methanol are heated together under reflux for 5 hours. The mixture is then concentrated and the residue is taken up in water. The solution is washed with ethyl acetate and the aqueous phase is acidified using conc. HCl (pH 1). The precipitate is filtered off with suction and dried.

Yield 14.4 g (80.6% of theory), m.p.: 140–142° C.

Similar to this method, and/or according to the general preparation procedures, the following compounds of the formula (XVII) are obtained:

TABLE 7

(XVII)

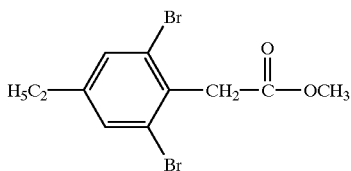

| Ex. No. | W | X | Y | Z | m.p. ° C. |
|---|---|---|---|---|---|
| XVII-2 | Br | Cl | C₂H₅ | H | 147 |
| XVII-3 | Cl | Cl | C₂H₅ | H | 146 |
| XVII-4 | H | Cl | C₂H₅ | H | 89–91 |
| XVII-5 | H | Br | C₂H₅ | H | 109 |
| XVII-6 | Br | Br | i-C₃H₇ | H | 154–155 |
| XVII-7 | H | CH₃ | Cl | Cl | 103 |

EXAMPLE (XVIII-1)

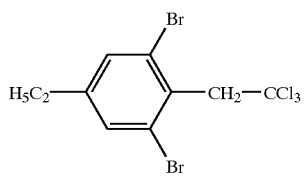

With cooling, 9.1 ml of 30% strength sodium methoxide are added dropwise to 5 g (94.4% strength, 0.0119 mol) of the compound of Example (XIX-1) in 5 ml of methanol, and the mixture is stirred under reflux for 5 hours. After cooling, 0.01 ml of concentrated sulphuric acid are added dropwise, and the mixture is stirred under reflux for 1 hour. The mixture is then concentrated and the residue is taken up in water. The solution is extracted with methylene chloride, dried and concentrated.

Yield 1.80 g (43% of theory), oil.

Similar to this method, and/or according to the general preparation procedures, the following compounds of the formula (XVIII) are obtained:

TABLE 8

(XVIII)

| Ex. No. | W | X | Y | Z | R⁸ | b.p. ° C. | (mbar) |
|---|---|---|---|---|---|---|---|
| XVIII-2 | Br | Cl | C₂H₅ | H | CH₃ | 105 | 0.06 |
| XVIII-3 | Cl | Cl | C₂H₅ | H | CH₃ | 92–94 | 0.05 |
| XVIII-4 | H | Cl | C₂H₅ | H | CH₃ | 82 | 0.03 |
| XVIII-5 | H | Br | C₂H₅ | H | CH₃ | 135 | 0.15 |
| XVIII-6 | Br | Br | i-C₃H₇ | H | CH₃ | oil* | |
| XVIII-7 | H | CH₃ | Cl | Cl | CH₃ | oil* | |

*After chromatographic purification, these compounds were directly reacted to give the corresponding acids of the formulae (XVII-6) and (XVII-7).

EXAMPLE (XIX-1)

140 ml (17.4 mol) of 1,1-dichloroethane and then 320 g (1.147 mol) of the compound of Example (XX-1) in 342 ml of anhydrous acetonitrile are added drop-wise to 208 ml (1.746 mol) of butyl nitrite in 684 ml of anhydrous acetonitrile. The mixture is stirred at room temperature overnight and then poured into 4.6 l of 20% strength HCl. The mixture is extracted with MTB ether and the organic phase is washed with 2 l of water, dried and concentrated.

Yield 434 g. The crude product reacted further without any further purification.

Similar to this method, and/or according to the general preparation procedures, the following compounds of the formula (XIX) are obtained:

TABLE 9

(XIX)

| Ex. No. | W | X | Y | Z | |
|---|---|---|---|---|---|
| XIX-2 | Br | Cl | C₂H₅ | H | oil* |
| XIX-3 | Cl | Cl | C₂H₅ | H | oil* |
| XIX-4 | H | Cl | C₂H₅ | H | oil* |
| XIX-5 | H | Br | C₂H₅ | H | GC/MS: 314, 316, 318 12%, 14%, 12% 199 (100%) 197 (98%) |
| XIX-6 | Br | Br | i-C₃H₇ | H | oil* |
| XIX-7 | H | CH₃ | Cl | Cl | oil* |

*The crude mixtures were directly employed for the alcoholysis for preparing the compounds of the formula (XVIII).

EXAMPLE (XX-1)

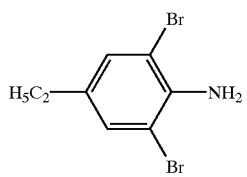

At 10–30° C., 397 g (2.48 mol) of bromine in 744 ml of glacial acetic acid are added dropwise to 150 g (1.24 mol) of 4-ethylaniline in 1990 ml of glacial acetic acid, and the mixture is stirred at 30° C. for another 3 hours. The mixture is then diluted with water and made alkaline using 25% strength ammonia solution. The precipitate is filtered off with suction, taken up in methylene chloride, dried and concentrated.

Yield 320.0 g (93% of theory), m.p.: 74° C.

EXAMPLE (XX-2)

Using the method of Example (XX-1) the compound of the formula

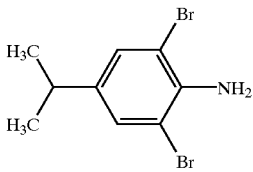

is obtained
M.p.: 48° C.

EXAMPLE (XXII-1)

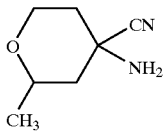

At room temperature, 30.5 g (0.27 mol) of 2-methyl-tetrahydropyran-4-one (preparation see further below) are added dropwise to a mixture comprising 50.9 g (0.75 mol) of 25% strength ammonia solution, 17.2 g (0.32 mol) of ammonium chloride and 15.7 g (0.32 mol) of sodium cyanide in 48 ml of water and the mixture is stirred at 45° C. overnight. Customary work-up gives 29.1 g (77% of theory) of the end product as an oil.

EXAMPLE (XXII-2)

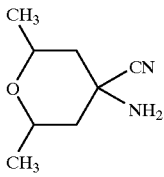

This compound is obtained in a similar manner as a brown oil.

EXAMPLE: COMPOUND OF THE FORMULA

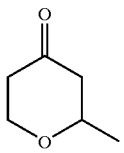

(2-methyl-tetrahydropyran-4-one)

At a temperature of approximately 100° C., 364.37 g of the compound of the formula $ClCH_2CH_2COCH_2CHClCH_3$ (preparation see the next example) are added dropwise over a period of approximately 75 minutes to 552.72 g (3.54 mol) of $NaH_2PO_4 \times 2H_2O$ and 179.7 g (1.55 mol) of 85% strength o-phosphoric acid in 5500 ml of water, and the mixture is stirred at 100° C. for a further 8 hours.

The mixture is cooled to approximately 0° C. and 10 molar NaOH is added dropwise until a pH of 5 to 6 is reached. 1500 ml of methylene chloride are added and the resulting salt is filtered off with suction and the aqueous phase is extracted 3× with 1000 ml of methylene chloride each time. The organic phase is dried, concentrated and distilled.

Yield: 119.6 g (55% of theory), b.p.: 62° C./15 mbar.

EXAMPLE: COMPOUND OF THE FORMULA
$ClCH_2CH_2COCH_2CHClCH_3$

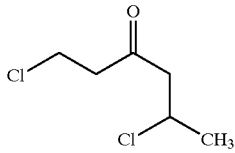

At room temperature, 507.88 g of 3-chloropropionyl chloride are added dropwise over a period of 15 minutes to 758.08 g (5.6 mol) of $AlCl_3$ in 560 ml of methylene chloride, and 189 g (4.5 mol) of propylene are introduced into this mixture at approximately 28 to 30° C. over a period of approximately 3 hours.

The reaction mixture is decanted off from excess $AlCl_3$ and, at 0 to 10° C., slowly added dropwise to a mixture of 508 ml of methylene chloride and 2032 ml of 1N HCl.

The organic phase is separated off, washed 3 times with 500 ml of water each time, dried and concentrated.

Yield: 470 g (70% of theory).

USE EXAMPLES

Example A

Myzus Test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested by peach aphids (*Myzus persicae*) are treated by being dipped into the preparation of active compound of the desired concentration.

After the desired period of time, the kill in % is determined. 100% means that all aphids have been killed; 0% means that none of the aphids have been killed.

In this test, at an exemplary active compound concentration of 0.1%, for example the compounds of Examples I-a-9, I-a-10, I-a-12, I-a-14, I-a-15, I-a-16, I-c-8, I-b-17, I-a-18, I-a-19, I-a-20, I-a-21, I-c-11 and I-c-12 effected a kill of in each case 100% after 6 days.

Example B

| Nephotettix test | |
|---|---|
| Solvent: | 20 parts of weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of active compound of the desired concentration and are populated with green rice leaf hoppers (*Nephotettix cincticeps*) while the seedlings are still moist.

After the desired period of time, the kill in % is determined. 100% means that all leaf hoppers have been killed; 0.1% means that none of the leaf hoppers have been killed.

In this test, at an exemplary active compound concentration of 0.1%, for example the compounds of Examples I-b-2, I-b-4, I-c-3, I-b-5, I-b-1, I-c-1, I-b-6, I-b-7, I-c-4, I-a-7, I-b-8, I-b-11, I-c-5, I-c-7, I-b-17, I-c-11, I-a-22, I-b-22, I-b-23 and I-b-24 effect in each case a kill of 100% after 6 days.

Example C

| *Phaedon larvae* test | |
|---|---|
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, at an exemplary active compound concentration of 0.1%, for example the compounds of Examples I-b-8, I-b-22, I-b-23, I-c-13, I-b-4, I-c-3, I-a-7 and I-a-8 effected a kill of in each case 100% after 7 days.

Example D

| *Spodoptera frugiperda* test | |
|---|---|
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with caterpillars of the owlet moth (*Spodoptera frugiperda*) while the leaves are still moist.

After the desired period of time, the kill, in % is determined. 100% means that all caterpillars have been killed; 0% means that none of the caterpillars have been killed.

In this test, at an exemplary active compound concentration of 0.1%, for example the compounds of Examples I-c-3, I-a-14, I-c-15, I-a-20, I-c-13 and I-b-24 effected a kill of in each case 100% after 7 days.

Example E

| Tetranychus test (OP-resistant/dip treatment) | |
|---|---|
| Solvent: | 3 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested by all stages of the greenhouse red spider mite *Tetranychus urticae* are dipped into a preparation of active compound of the desired concentration.

After the desired period of time, the kill in % is determined. 100% means that all spider mites have been killed; 0% means that none of the spider mites have been killed.

In this test, at an exemplary active compound concentration of 0.1%, for example the compounds of Examples I-b-2, I-b-3, I-b-4, I-c-3, I-a4, I-c-1, I-b-7, I-c-4, I-a-7, I-a-9 and I-b-8 had an effect of in each case 100% after 14 days, and the compounds of Examples I-b-15, I-b-16, I-b-17, I-b-22 and I-c-13 had this effect at an exemplary active compound concentration of 0.02%.

Example F

| Critical concentration test/root-systemic action | |
|---|---|
| Test insect: | *Aphis fabae* |
| Solvent: | 4 parts by weight of acetone |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The treated soil is transferred into pots and these are planted with pregerminated broad beans. The active compound can in this way be taken up from the soil by the roots of the plants and be transported into the leaves.

To demonstrate the root-systemic effect, the leaves are populated with the above-mentioned test animals after 7 days. After a further 6 days, evaluation is carried out by counting or estimating the dead animals. The root-systemic action of the active compound is deduced from the mortality figures. It is 100% if all the test animals have been killed and 0% if just as many test insects are still alive as in the case of the untreated control.

In this test, at an exemplary active compound concentration of 20 ppm, for example the compounds of Examples I-a-1, I-b4, I-a-4, I-b-5, I-a-16, I-b-1, I-b-3, I-c-1, I-c-2, I-b-17, I-b-10, I-a-16 and I-b-25 had an effect of in each case 100%.

Example G

| Critical concentration test/root-systemic action | |
|---|---|
| Test insect: | *Myzus persicae* |
| Solvent: | 4 parts by weight of acetone |
| Emulsifier: | 1 part of weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

The preparation of active compound is intimately mixed with soil. The concentration of the active compound in the preparation is of practically no importance here, only the amount by weight of active compound per unit volume of soil, which is given in a ppm (=mg/l), being decisive. The treated soil is transferred into pots and these are planted with peppers at the cotyledon stage. The active compound can in this way be taken up from the soil by the roots of the plants and be transported into the leaves.

To demonstrate the root-systemic effect, the leaves are populated with the above-mentioned test animals after 7 days. After a further 6 days, evaluation is carried out by counting or estimating the dead animals. The root-systemic action of the active compound is deduced from the mortality figures. It is 100% if all the test animals have been killed and 0% if just as many test insects are still alive as in the case of the untreated control.

In this test, at an exemplary active compound concentration of 20 ppm, for example the compounds of examples I-b-10, I-a-16 and 1-b-25 had an effect of in each case 100%.

What is claimed is:
1. Compound of the formula (I)

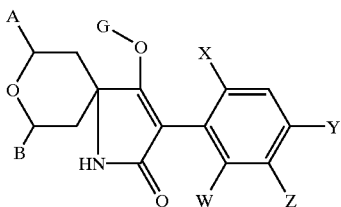

(I)

in which
W represents hydrogen, cyano, nitro, halogen, alkyl, alkenyl, alkinyl, alkoxy, halogenoalkyl, halogenoalkoxy or represents phenyl, phenoxy, phenylthio, phenylalkoxy or phenylalkylthio, each of which is optionally substituted, X represents halogen, alkyl, alkenyl, alkinyl, alkoxy, alkenyloxy, halogenoalkyl, halogenoalkoxy, halogenoalkenyloxy, cyano, nitro or represents phenyl, phenoxy, phenylthio, phenylalkyloxy or phenylalkylthio, each of which is optionally substituted, Y represents hydrogen, halogen, alkyl, alkoxy, halogenoalkyl, halogenoalkoxy, cyano or nitro, Z represents hydrogen, halogen, alkyl, alkoxy, halogenoalkyl, halogenoalkoxy, hydroxyl, cyano, nitro or represents phenoxy, phenylthio, 5- or 6-membered hetaryloxy, 5- or 6-membered hetarylthio, phenylalkyloxy or phenylalkylthio, each of which is optionally substituted, A represents alkyl or optionally substituted phenyl,
B represents hydrogen or alkyl,
G represents hydrogen (a) or one of the radicals (b)
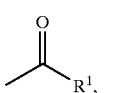

(c)
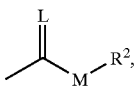

(d)
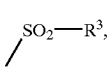

(e)
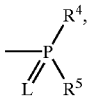

(f)
E, or (g)
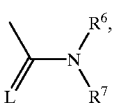

in which
E represents a metal ion equivalent or an ammonium ion,
L represents oxygen or sulphur,
M represents oxygen or sulphur,
$R^1$ represents alkyl, alkenyl, alkoxyalkyl, alkylthioalkyl or polyalkoxyalkyl, each of which is optionally substituted by halogen or cyano, or represents cycloalkyl or heterocyclyl, each of which is optionally substituted by halogen, alkyl or alkoxy, or represents phenyl, phenylalkyl, hetaryl, phenoxyalkyl or hetaryloxyalkyl, each of which is optionally substituted,
$R^2$ represents alkyl, alkenyl, alkoxyalkyl or polyalkoxyalkyl, each of which is optionally substituted by halogen or cyano, or represents cycloalkyl, phenyl or benzyl, each of which is optionally substituted
$R^3$, $R^4$ and $R^5$ independently of one another each represent alkyl, alkoxy, alkylamino, dialkylamino, alkylthio, alkenylthio or cycloalkylthio, each of which is optionally substituted by halogen, or represent phenyl, benzyl, phenoxy or phenylthio, each of which is optionally substituted,
$R^6$ and $R^7$ independently of one another each represent hydrogen, represent alkyl, cycloalkyl, alkenyl, alkoxy, alkoxyalkyl, each of which is optionally substituted by halogen or cyano, represent phenyl or benzyl, each of which is optionally substituted, or together with the linking N atom form a cycle which optionally contains oxygen or sulphur and which is optionally substituted.

2. A compound of the formula (I) according to claim 1, in which
W represents hydrogen, nitro, cyano, halogen, $C_1$–$C_6$-alkyl, $C_2$–$C_6$-alkenyl, $C_2$–$C_6$-alkinyl, $C_1$–$C_6$-alkoxy, $C_1$–$C_4$-halogenoalkyl or $C_1$–$C_4$-halogenoalkoxy,
X represents halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_4$-halogenoalkyl, $C_1$–$C_4$-halogenoalkoxy, $C_2$–$C_6$-halogenoalkenyloxy, cyano, nitro or represents phenyl, phenoxy, phenylthio, phenyl-$C_1$–$C_4$-alkoxy or phenyl-$C_1$–$C_4$-alkylthio, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, Y represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, Z represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, hydroxyl, cyano, nitro or represents phenoxy, phenylthio, thiazolyloxy, pyridinyloxy, pyrimidyloxy, pyrazolyloxy, phenyl-$C_1$–$C_4$-alkyloxy or phenyl-$C_1$–$C_4$-alkylthio, each of which is optionally substituted by halogen, $C_1$–$C_4$-alkyl, $C_1$–$C_4$-alkoxy, $C_1$–$C_4$-halogenoalkyl, $C_1$–$C_4$-halogenalkoxy, nitro or cyano, A represents $C_1$–$C_6$-alkyl or represents phenyl which is optionally substituted by halogen, $C_1$–$C_4$-alkyl, $C_1$–$C_4$-alkoxy, nitro or cyano, B represents hydrogen or $C_1$–$C_6$-alkyl.

G represents hydrogen (a) or represents one of the radicals

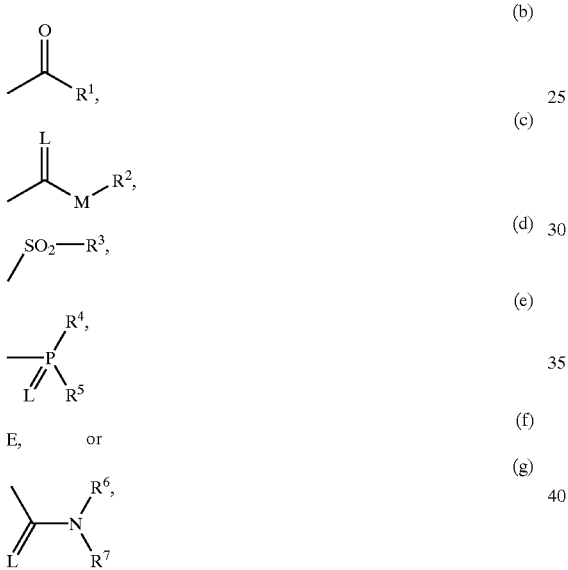

in which

E represents a metal ion equivalent or an ammonium ion,

L represents oxygen or sulphur and

M represents oxygen or sulphur, $R^1$ represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl each of which is optionally substituted by halogen or cyano, or represents $C_3$–$C_8$-cycloalkyl in which optionally one or two not directly adjacent methylene groups are replaced by oxygen and/or sulphur and which is optionally substituted by halogen, $C_1$–$C_6$-alkyl or $C_1$–$C_6$-alkoxy, represents phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulfonyl, represents phenyl-$C_1$–$C_6$-alkyl which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, represents 5- or 6-membered hetaryl having one or two hetero atoms selected from the group consisting of oxygen, sulphur and nitrogen which is optionally substituted by halogen or $C_1$–$C_6$-alkyl, represents phenoxy-$C_1$–$C_6$-alkyl which is optionally substituted by halogen or $C_1$–$C_6$-alkyl or represents 5- or 6-membered hetaryloxy-$C_1$–$C_6$-alkyl having one or two hetero atoms selected from the group consisting of oxygen, sulphur and nitrogen which is optionally substituted by halogen, amino or $C_1$–$C_6$-alkyl.

$R^2$ represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally substituted by halogen or cyano, represents $C_3$–$C_8$-cycloalkyl which is optionally substituted by halogen, $C_1$–$C_6$-alkyl or $C_1$–$C_6$-alkoxy or represents phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy, $R^3$ represents $C_1$–$C_8$-alkyl which is optionally substituted by halogen or represents phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^4$ and $R^5$ independently of one another represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_3$–$C_8$-alkenylthio, each of which is optionally substituted by halogen, or represents phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^6$ and $R^7$ independently of one another represent hydrogen, represent $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_2$–$C_8$-alkyl, each of which is optionally substituted by halogen or cyano or represents phenyl or benzyl, each of which is optionally substituted by halogen, $C_1$–$C_8$-alkyl, $C_1$–$C_8$-halogenoalkyl or $C_1$–$C_8$-alkoxy, or together represent a $C_3$–$C_6$-alkylene radical in which optionally one methylene group is replaced by oxygen or sulphur and which is optionally substituted by $C_1$–$C_6$-alkyl.

3. A compound of the formula (I) according to claim 1, in which

W represents hydrogen, nitro, cyano, fluorine, chlorine, bromine, $C_1$–$C_4$-alkyl, $C_1$–$C_4$-alkoxy, $C_1$–$C_2$-halogenoalkyl or $C_1$–$C_2$-halogenoalkoxy, X represents fluorine, chlorine, bromine, $C_1$–$C_4$-alkyl, $C_1$–$C_4$-alkoxy, $C_3$–$C_4$-alkenyloxy, $C_1$–$C_2$-halogenoalkyl, $C_1$–$C_2$-halogenoalkoxy, $C_2$–$C_4$-halogenoalkenyloxy, cyano, nitro or represents phenyl or benzyloxy, each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, Y represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, Z represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxyl, cyano, nitro or represents phenoxy or benzyloxy, each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, A represents $C_1$–$C_4$-alkyl or represents phenyl, B represents hydrogen, methyl or ethyl, G represents hydrogen (a) or represents one of the radicals

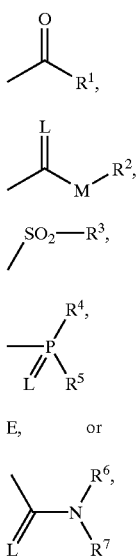

in which

E represents a metal ion equivalent or an ammonium ion,

L represents oxygen or sulphur and

M represents oxygen or sulphur, $R^1$ represents $C_1$–$C_{16}$-alkyl, $C_2$-$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl, each of which is optionally substituted by fluorine, chlorine, or represents $C_3$–$C_7$-cycloalkyl in which optionally one or two not directly adjacent methylene groups are replaced by oxygen and/or sulphur and which is optionally substituted by fluorine, chlorine, $C_1$–$C_5$-alkyl or $C_1$–$C_5$-alkoxy, represents phenyl, which is optionally substituted by fluorine, chlorine, bromine, cyano, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl, represents phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, represents pyrazolyl, thiazolyl, pyridyl, pyrimidyl, furanyl or thienyl, each of which is optionally substituted by fluorine, chlorine, bromine or $C_1$–$C_4$-alkyl, represents phenoxy-$C_1$–$C_5$-alkyl which is optionally substituted by fluorine, chlorine, bromine or $C_1$–$C_4$-alkyl or represents pyridyloxy-$C_1$–$C_5$-alkyl, pyrimidyloxy-$C_1$–$C_5$-alkyl or thiazolyloxy-$C_1$–$C_5$-alkyl, each of which is optionally substituted by fluorine, chlorine, bromine, amino or $C_1$–$C_4$-alkyl, $R^2$ represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, each of which is optionally substituted by fluorine or chlorine, represents $C_3$–$C_7$-cycloalkyl which is optionally substituted by fluorine, chlorine, $C_1$–$C_4$-alkyl or $C_1$–$C_4$-alkoxy or represents phenyl or benzyl, each of which is optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy, $R^3$ represents $C_1$–$C_6$-alkyl which is optionally substituted by fluorine or chlorine or represents phenyl or benzyl, each of which is optionally substituted by fluorine, chlorine, bromine, $C_1$–$C_4$-alkyl, $C_1$–$C_4$-alkoxy, $C_1$–$C_2$-halogenoalkoxy, $C_1$–$C_2$-halogenoalkyl, cyano or nitro, $R^4$ and $R^5$ independently of one another represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio, each of which is optionally substituted by fluorine or chlorine, or represent phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, $R^6$ and $R^7$ independently of one another particularly preferably represent hydrogen, represent $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, each of which is optionally substituted by fluorine or chlorine, or represent phenyl or benzyl, each of which is optionally substituted by fluorine, chlorine, bromine, $C_1$–$C_5$-halogenoalkyl, $C_1$–$C_5$-alkyl or $C_1$–$C_5$-alkoxy, or together represent a $C_3$–$C_6$-alkylene radical in which optionally one methylene group is replaced by oxygen or sulphur and which is optionally substituted by $C_1$–$C_4$-alkyl.

4. A compound of the formula (I) according to claim 1, in which

W represents hydrogen, nitro, cyano, fluorine, chlorine, bromine, methyl, ethyl, n-propyl, isopropyl, n-butyl, isobutyl, methoxy, ethoxy, n-propoxy, isopropoxy, trifluoromethyl, difluoromethoxy or trifluoromethoxy, X represents fluorine, chlorine, bromine, methyl, ethyl, n-propyl, isopropyl, n-butyl, isobutyl, methoxy, ethoxy, n-propoxy, isopropoxy, trifluoromethyl, trifluoromethoxy, difluoromethoxy, cyano or nitro, Y represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy, difluoromethoxy, cyano or nitro, Z represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy, difluoromethoxy, cyano or nitro, A represents methyl or ethyl, B represents hydrogen or methyl, G represents hydrogen (a) or represents one of the radicals

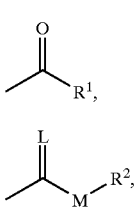

-continued

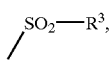

(d)

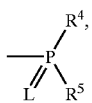

(e)

E, or (f)

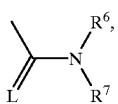

(g)

in which

E represents a metal ion equivalent or an ammonium ion,

L represents oxygen or sulphur and

M represents oxygen or sulphur, $R^1$ represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl, each of which is optionally substituted by fluorine or chlorine, or represents $C_3$–$C_6$-cycloalkyl in which optionally one or two not directly adjacent methylene groups are replaced by oxygen and/or sulphur and which is optionally substituted by fluorine, chlorine, methyl, ethyl, n-propyl, i-propyl, n-butyl, i-butyl, tert-butyl, methoxy, ethoxy, n-propoxy or isopropoxy, represents phenyl which is optionally substituted by fluorine, chlorine, bromine, cyano, nitro, methyl, ethyl, n-propyl, i-propyl, methoxy, ethoxy, trifluoromethyl, trifluoromethoxy, methylthio, ethylthio, methylsulphonyl or ethylsulphonyl, represents benzyl which is optionally substituted by fluorine, chlorine, bromine, methyl, ethyl, n-propyl, i-propyl, methoxy, ethoxy, trifluoromethyl or trifluoromethoxy, represents furanyl, thienyl or pyridyl, each of which is optionally substituted by fluorine, chlorine, bromine, methyl or ethyl, represents phenoxy-$C_1$–$C_4$-alkyl which is optionally substituted by fluorine, chlorine, methyl or ethyl or represents pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl, $R^2$ represents $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, each of which is optionally substituted by fluorine or chlorine, represents $C_3$–$C_6$-cycloalkyl which is optionally substituted by fluorine, chlorine, methyl, ethyl, n-propyl, isopropyl or methoxy, or represents phenyl or benzyl, each of which is optionally substituted by fluorine, chlorine, cyano, nitro, methyl, ethyl, n-propyl, i-propyl, methoxy, ethoxy, trifluoromethyl or trifluoromethoxy, $R^3$ represents methyl, ethyl, n-propyl, isopropyl, n-butyl, tert-butyl, each of which is optionally substituted by fluorine or chlorine, or represents phenyl or benzyl, each of which is optionally substituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio, each of which is optionally substituted by fluorine or chlorine, or represent phenyl, phenoxy or phenylthio, each of which is optionally substituted by fluorine, chlorine, bromine, nitro, cyano, methyl, methoxy, trifluoromethyl or trifluoromethoxy and $R^6$ and $R^7$ independently of one another represent hydrogen, represent $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_2$–$C_4$-alkyl, each of which is optionally substituted by fluorine or chlorine, or represent phenyl or benzyl, each of which is optionally substituted by fluorine, chlorine, bromine, methyl, methoxy or trifluoromethyl, or together represent a $C_5$–$C_6$-alkylene radical in which optionally one methylene group is replaced by oxygen or sulphur and which is optionally substituted by methyl or ethyl.

5. A process for preparing compounds of the formula (I) according to claim 1, wherein (A) compounds of the formula (I-a)

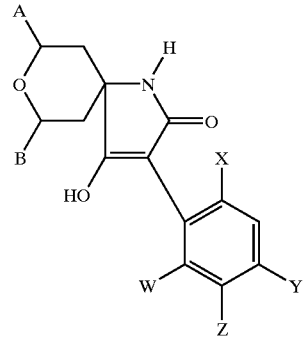

(I-a)

in which

A, B, W, X, Y and Z are each as defined in claim 1, are obtained when compounds of the formula (II)

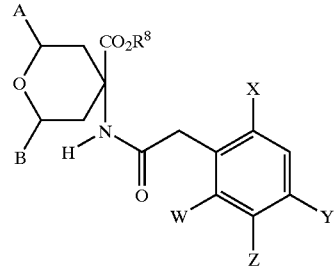

(II)

in which

A, B, W, X, Y and Z are each as defined in claim 1 and $R^8$ represents alkyl, are intramolecularly condensed in the presence of a diluent and in the presence of a base and are, optionally, subsequently (Bα) reacted with acyl halides of the formula (III)

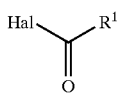 (III)

in which
R¹ is as defined in claim 1 and
Hal represents halogen or
β) reacted with carboxylic anhydrides of the formula (IV)

$$R^1-CO-O-CO-R^1 \quad (IV)$$

in which
R¹ is as defined above,
optionally in the presence of a diluent and/or optionally in the presence of an acid binder; or
(C) reacted with chloroformic esters or chloroformic thioesters of the formula (V)

$$R^2-M-CO-Cl \quad (V)$$

in which
R² and M are each as defined in claim 1,
optionally in the presence of a diluent and/or optionally in the presence of an acid binder; or
(D) reacted with chloromonothioformic esters or chlorodithioformic esters of the formula (VI)

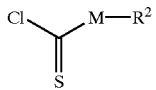 (VI)

in which
M and R² are each as defined above,
optionally in the presence of a diluent and/or optionally in the presence of an acid binder; or
(E) reacted with sulphonyl chlorides of the formula (VII)

$$R^3-SO_2-Cl \quad (VII)$$

in which
R³ is as defined in claim 1,
optionally in the presence of a diluent and/or optionally in the presence of an acid binder; or
(F) reacted with phosphorus compounds of the formula (VIII)

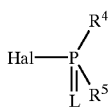 (VIII)

in which
L, R⁴ and R⁵ are each as defined in claim 1 and Hal represents halogen,
optionally in the presence of a diluent and/or optionally in the presence of an acid binder; or
(G) reacted with metal compounds or amines of the formulae (IX) or (X)

$$Me(OR^9)_t \quad (IX)$$

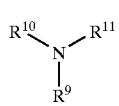 (X)

in which
Me represents a mono- or divalent metal,
t represents the number 1 or 2 and R⁹, R¹⁰, R¹¹ independently of one another each represent hydrogen or alkyl,
optionally in the presence of a diluent; or
(Hα) reacted with isocyanates or isothiocyanates of the formula (XI)

$$R^6-N=C=L \quad (XI)$$

in which
R⁶ and L are each as defined in claim 1,
optionally in the presence of a diluent and/or optionally in the presence of a catalyst; or
β) reacted with carbamoyl chlorides or thiocarbamoyl chlorides of the formula (XII)

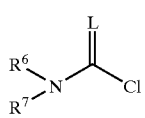 (XII)

in which
L, R⁶ and R⁷ are each as defined in claim 1, optionally in the presence of a diluent and/or optionally in the presence of an acid binder.

6. A pesticide or herbicide comprising a compound of the formula (I) according to claim 1 and an extender and/or a surfactant.

7. A method for controlling pests and weeds comprising applying a compound of the formula (I) according to claim 1 on pests or weeds and/or their habitat.

8. A process for preparing pesticides and herbicides, comprising mixing a compound of the formula (I) according to claim 1 with an extender and/or a surfactant.

* * * * *